(12) United States Patent
Anderson et al.

(10) Patent No.: US 9,308,120 B2
(45) Date of Patent: Apr. 12, 2016

(54) METHODS AND DEVICES FOR SELECTIVE DISRUPTION OF FATTY TISSUE BY CONTROLLED COOLING

(75) Inventors: Richard R. Anderson, Boston, MA (US); Dieter Manstein, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 1878 days.

(21) Appl. No.: 11/434,478

(22) Filed: May 15, 2006

(65) Prior Publication Data

US 2007/0010861 A1 Jan. 11, 2007

Related U.S. Application Data

(62) Division of application No. 10/391,221, filed on Mar. 17, 2003, now Pat. No. 7,367,341.

(60) Provisional application No. 60/365,662, filed on Mar. 15, 2002.

(51) Int. Cl.
*A61F 7/00* (2006.01)
*A61B 5/00* (2006.01)
(Continued)

(52) U.S. Cl.
CPC . *A61F 7/00* (2013.01); *A61B 5/415* (2013.01); *A61B 5/6804* (2013.01); *A61B 18/02* (2013.01); *A61F 7/10* (2013.01); *A61H 23/00* (2013.01); *A61B 2018/0237* (2013.01); *A61B 2018/0262* (2013.01); *A61F 2007/0054* (2013.01); *A61F 2007/0056* (2013.01); *A61F 2007/0075* (2013.01); *A61F 2007/0082* (2013.01); *A61F 2007/0094* (2013.01);
(Continued)

(58) Field of Classification Search
CPC .............. A61F 7/10; A61F 2007/0075; A61F 2007/029; A61F 2007/0056; A61F 2007/0239; A61B 18/0206; A61H 23/00
USPC ........................................ 606/20–22; 607/108
See application file for complete search history.

(56) References Cited

U.S. PATENT DOCUMENTS 3,093,135 A 6/1963 Hirschhorn
3,502,080 A 3/1970 Hirschhorn
(Continued)

FOREIGN PATENT DOCUMENTS

CH 333982 11/1958
DE 532976 5/1974
(Continued)

OTHER PUBLICATIONS

Nagore et al. "*Lipoatrophia semicircularis*—a traumatic panniculitis: Report of seven cases and review of the literature." Journal of the American Academy of Dermatology: 879-881 (1998).
(Continued)

*Primary Examiner* — Kaitlyn Smith
(74) *Attorney, Agent, or Firm* — Saul Ewing LLP; Brian R. Landry, Esq.; Peter C. Lauro, Esq.

(57) ABSTRACT

The present invention relates to methods for use in the selective disruption of lipid-rich cells by controlled cooling. The present invention further relates to a device for use in carrying out the methods for selective disruption of lipid-rich cells by controlled cooling.

42 Claims, 27 Drawing Sheets

(51) Int. Cl.
  *A61B 18/02* (2006.01)
  *A61F 7/10* (2006.01)
  *A61H 23/00* (2006.01)
  *A61F 7/02* (2006.01)
(52) U.S. Cl.
  CPC .. *A61F 2007/0096* (2013.01); *A61F 2007/029* (2013.01); *A61F 2007/0239* (2013.01)

(56) References Cited

U.S. PATENT DOCUMENTS

| | | |
|---|---|---|
| 3,942,519 A | 3/1976 | Shock |
| 3,986,385 A | 10/1976 | Johnston et al. |
| 4,202,336 A | 5/1980 | van Gerven et al. |
| 4,381,009 A | 4/1983 | Del Bon et al. |
| 4,483,341 A | 11/1984 | Witteles |
| 4,528,979 A | 7/1985 | Marchenko et al. |
| 4,531,524 A | 7/1985 | Mioduski |
| 4,585,002 A | 4/1986 | Kissin |
| 4,614,191 A | 9/1986 | Perler |
| 4,644,955 A | 2/1987 | Mioduski |
| 4,700,701 A | 10/1987 | Montaldi |
| 4,718,429 A * | 1/1988 | Smidt ............... 607/104 |
| 4,741,338 A | 5/1988 | Miyamae |
| 4,802,475 A | 2/1989 | Weshahy et al. |
| 4,832,022 A | 5/1989 | Tjulkov et al. |
| 4,869,250 A | 9/1989 | Bitterly |
| 4,905,697 A * | 3/1990 | Heggs et al. ............... 607/18 |
| 4,961,422 A | 10/1990 | Marchosky et al. |
| 5,007,433 A | 4/1991 | Hermsdorffer et al. |
| 5,084,671 A | 1/1992 | Miyata et al. |
| 5,108,390 A | 4/1992 | Potocky et al. |
| 5,119,674 A | 6/1992 | Nielsen et al. |
| 5,143,063 A | 9/1992 | Fellner |
| 5,148,804 A | 9/1992 | Hill et al. |
| 5,169,384 A | 12/1992 | Bosniak et al. |
| 5,197,466 A | 3/1993 | Marchosky et al. |
| 5,207,674 A | 5/1993 | Hamilton |
| 5,277,030 A | 1/1994 | Miller |
| 5,330,745 A | 7/1994 | McDow |
| 5,339,541 A | 8/1994 | Owens |
| 5,351,677 A | 10/1994 | Kami et al. |
| 5,358,467 A | 10/1994 | Milstein et al. |
| 5,411,541 A | 5/1995 | Bell et al. |
| 5,507,790 A | 4/1996 | Weiss |
| 5,531,742 A | 7/1996 | Barken |
| 5,628,769 A | 5/1997 | Saringer |
| 5,634,940 A | 6/1997 | Panyard |
| 5,647,868 A | 7/1997 | Chinn |
| 5,654,546 A | 8/1997 | Lindsay |
| 5,660,836 A | 8/1997 | Knowlton |
| 5,665,053 A | 9/1997 | Jacobs |
| 5,672,172 A | 9/1997 | Zupkas |
| 5,725,483 A | 3/1998 | Podolsky |
| 5,733,280 A | 3/1998 | Avitall |
| 5,741,248 A | 4/1998 | Stern et al. |
| 5,755,663 A | 5/1998 | Larsen et al. |
| 5,755,753 A | 5/1998 | Knowlton |
| 5,759,182 A | 6/1998 | Varney et al. |
| 5,769,879 A | 6/1998 | Richards et al. |
| 5,830,208 A | 11/1998 | Muller |
| 5,833,685 A | 11/1998 | Tortal et al. |
| 5,871,524 A | 2/1999 | Knowlton |
| 5,895,418 A | 4/1999 | Saringer et al. |
| 5,902,256 A | 5/1999 | Benaron |
| 5,919,219 A | 7/1999 | Knowlton |
| 5,948,011 A | 9/1999 | Knowlton |
| 5,964,749 A | 10/1999 | Eckhouse et al. |
| 5,967,976 A | 10/1999 | Larsen et al. |
| 6,017,337 A * | 1/2000 | Pira ............... 606/20 |
| 6,023,932 A | 2/2000 | Johnston et al. |
| 6,032,675 A | 3/2000 | Rubinsky |
| 6,102,885 A | 8/2000 | Bass |
| 6,120,519 A | 9/2000 | Weber et al. |
| 6,241,753 B1 | 6/2001 | Knowlton |
| 6,264,649 B1 * | 7/2001 | Whitcroft et al. ............... 606/22 |
| 6,273,884 B1 | 8/2001 | Altshuler et al. |
| 6,311,090 B1 | 10/2001 | Knowlton |
| 6,350,276 B1 * | 2/2002 | Knowlton ............... 607/104 |
| 6,354,297 B1 | 3/2002 | Eiseman |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,405,090 B1 | 6/2002 | Knowlton |
| 6,413,255 B1 | 7/2002 | Stern |
| 6,425,912 B1 | 7/2002 | Knowlton |
| 6,430,446 B1 | 8/2002 | Knowlton |
| 6,438,424 B1 | 8/2002 | Knowlton |
| 6,453,202 B1 | 9/2002 | Knowlton |
| 6,461,378 B1 | 10/2002 | Knowlton |
| 6,470,216 B1 | 10/2002 | Knowlton |
| 6,471,693 B1 | 10/2002 | Carroll et al. |
| 6,494,844 B1 | 12/2002 | Van Bladel et al. |
| 6,497,721 B2 | 12/2002 | Ginsburg, incapacited et al. |
| 6,519,964 B2 | 2/2003 | Bieberich |
| 6,527,765 B2 | 3/2003 | Kelman et al. |
| 6,544,248 B1 | 4/2003 | Bass |
| 6,569,189 B1 | 5/2003 | Augustine et al. |
| 6,592,577 B2 | 7/2003 | Abboud et al. |
| 6,605,080 B1 | 8/2003 | Altshuler et al. |
| 6,626,854 B2 | 9/2003 | Friedman et al. |
| 6,635,053 B1 | 10/2003 | Lalonde et al. |
| 6,645,162 B2 | 11/2003 | Friedman et al. |
| 6,645,229 B2 | 11/2003 | Matsumura et al. |
| 6,648,904 B2 | 11/2003 | Altshuler et al. |
| 6,749,624 B2 | 6/2004 | Knowlton |
| 6,789,545 B2 | 9/2004 | Littrup et al. |
| 6,840,955 B2 | 1/2005 | Ein |
| 6,918,903 B2 | 7/2005 | Bass |
| 6,945,942 B2 | 9/2005 | Van Bladel et al. |
| 7,037,326 B2 | 5/2006 | Lee et al. |
| 7,276,058 B2 * | 10/2007 | Altshuler et al. ............... 606/9 |
| 7,367,341 B2 | 5/2008 | Anderson et al. |
| 7,613,523 B2 * | 11/2009 | Eggers et al. ............... 607/103 |
| 2001/0023364 A1 | 9/2001 | Ahn |
| 2002/0026226 A1 | 2/2002 | Ein |
| 2002/0049483 A1 | 4/2002 | Knowlton |
| 2002/0188286 A1 | 12/2002 | Quijano et al. |
| 2003/0069618 A1 | 4/2003 | Smith, III et al. |
| 2003/0100936 A1 | 5/2003 | Altshuler et al. |
| 2003/0109908 A1 | 6/2003 | Lachenbruch et al. |
| 2003/0114885 A1 * | 6/2003 | Nova et al. ............... 607/2 |
| 2003/0220674 A1 | 11/2003 | Anderson et al. |
| 2004/0049178 A1 | 3/2004 | Abboud et al. |
| 2004/0073079 A1 | 4/2004 | Altshuler et al. |
| 2004/0082886 A1 | 4/2004 | Timpson |
| 2004/0093042 A1 | 5/2004 | Altshuler et al. |
| 2004/0162596 A1 | 8/2004 | Altshuler et al. |
| 2004/0199226 A1 | 10/2004 | Shadduck |
| 2004/0210214 A1 * | 10/2004 | Knowlton ............... 606/41 |
| 2004/0210287 A1 | 10/2004 | Greene |
| 2004/0236252 A1 * | 11/2004 | Muzzi et al. ............... 601/1 |
| 2005/0251120 A1 | 11/2005 | Anderson et al. |
| 2006/0036300 A1 | 2/2006 | Kreindel |
| 2007/0010861 A1 * | 1/2007 | Anderson et al. ............... 607/96 |
| 2009/0171334 A1 * | 7/2009 | Elkins et al. ............... 606/21 |

FOREIGN PATENT DOCUMENTS

| | | |
|---|---|---|
| DE | 4213584 | 11/1992 |
| DE | 4213584 A1 | 11/1992 |
| DE | 4224595 | 1/1994 |
| DE | 4224595 A1 | 1/1994 |
| EP | 0263069 | 4/1988 |
| EP | 0397 043 A1 | 11/1990 |
| EP | 0397043 | 11/1990 |
| EP | 0406244 | 1/1991 |
| EP | 0 263 069 A2 | 4/1998 |
| FR | 854937 | 4/1940 |
| FR | 2744358 | 8/1997 |
| FR | 2767476 | 2/1999 |
| FR | 2776920 | 10/1999 |

(56) References Cited

FOREIGN PATENT DOCUMENTS

| FR | 2789893 | 8/2000 |
|---|---|---|
| FR | 2805989 | 9/2001 |
| GB | 313679 | 6/1929 |
| GB | 387960 | 2/1933 |
| GB | 2120944 | 12/1983 |
| GB | 2263872 A | 8/1993 |
| GB | 2286660 | 8/1995 |
| JP | 01223961 | 7/1989 |
| WO | WO 91/14417 | 10/1991 |
| WO | WO 96/23447 A1 | 8/1996 |
| WO | 97/24088 A1 | 7/1997 |
| WO | WO 98/31321 | 7/1998 |
| WO | WO 98/41157 | 9/1998 |
| WO | WO 99/09928 | 3/1999 |
| WO | WO 99/16502 | 4/1999 |
| WO | WO 99/49937 A1 | 10/1999 |
| WO | WO 00/44346 | 8/2000 |
| WO | WO 0044346 A1 * | 8/2000 |
| WO | 0100269 A1 | 1/2001 |
| WO | WO 01/34048 A1 | 5/2001 |
| WO | 03/078596 | 9/2003 |
| WO | WO 03/078596 | 9/2003 |
| WO | WO 2004/000098 | 12/2003 |
| WO | 2004080279 | 9/2004 |

OTHER PUBLICATIONS

Heller Page et al. "Temperature-dependent skin disorders." Journal of the American Academy of Dermatology 18(5); 1003-1019 (1988).
Shephard "Adaptation to Exercise in the Cold." Sports Medicine 2 : 59-71 (1985).
Henry et al. "Les Dermatoses Hivemales" Rev Med Liege 54:11, 864-866 (1999).
Nagao et al. "Dietary diacylglycerol suppresses accumulation of body fat compared to triacylglycerol in men a double-blind controlled trial." J Nutr Apr. 2000;130(4):792-7.
Lidagoster, MD et al. "Comparison of Autologous Fat Transfer in Fresh, Refrigerated, and Frozen Specimens: An Animal Model." Presented at the 16th Annual Meeting of the Northeastern Society of Plastic Surgeons: Burlington, VT; Sep. 30-Oct. 2, 1999; pp. 512-515.
Peterson et al. "Bilateral Fat Necrosis of the Scrotum." Urology Service, Department of Surgery, Dermatology Service, Department of Medicine and Department of Pediatrics, Letterman Army Medical Center, Presidio of San Francisco, Californa, vol. 116, December, The Journal of Urology, copyright 1976 by the Williams & Wilkins Co., pp. 825-826.
Hong, "Patterns of Ice Formation in Normal and Malignant Breast Tissue" Cryobiology 31, 109-120 (1994).
Ardevol "Cooling rates of tissue samples during freezing with liquid nitrogen" J. of Biochem. and Biophysical Methods 27, 77-86 (1993).
Holman "Variation in cryolesion penetration due to probe size and tissue thermal conductivity" Ann. Thorac. Surg. 53, 123-126 (1992).
Pech "Attenuation values, volume changes and artifacts in tissue due to freezing" Acta Radiologica 6, 779-782 (1987).
Hemmingsson "Attenuation in Human Muscle and Fat Tissue in Vivo and in Vitro" Acta Radiologica Daignosis 23, 149-151 (1982).
Gage "Current Progress in Cryosurgery" Cryobiology 25, 483-486 (1988).
Rubinsky "Cryosurgery: advances in the application of low temperatures to medicine" Int. J. Refrig. 190-199 (1991).
Pease "An Integrated Probe for Magnetic Resonance Imaging Monitored Skin Cryosurgery" Journal of Biomedical Engineering 117, 59-63, (1995).
Rabi "Metabolic adaptations in brown adipose tissue of the hamster in extreme ambient temperatures" American Journal of Physiology 231, 153-160 (1976).
Laugier, et al., "In Vivo Results with a New Device for Ultrasonic Monitoring of Pig Skin Cryosurgery: The Echographic Cryoprobe", The Society for Investigative Dermatology, Inc., vol. 111 (2), Aug. 1998.

Bondei, E. et al. "Disorders of Subcutaneous Tissue (Cold Panniculitis)," Dermatology in General Medicine Chapter 108, Section 16 1333-1334 (1993).
Burge, S.M. et al. "Hair Follicle Destruction and Regeneration in Guinea Pig Skin after Cutaneous Freeze Injury," Cryobiology, 27(2): 153-163 (1990).
Duncan, W. C. et al. "Cold Panniculitis," Arch Derm., 94:722-24 (1966).
Epstein, E. H. et al. "Popsicle Panniculitis" The New England Journal of Medicine, 282 (17): 966-67, (1970).
Kellum, R. E. et al. "Sclerema Neonatorum: Report of Case and Analysis of Subcutaneous and Epidermal-Dermal Lipids by Chromatographic Methods" Arch. Derm., 97: 372-380, (1968).
Koska, J. et al. "Endocrine Regulation of Subcutaneous Fat Metabolism During Cold Exposure in Humans," Ann. N.Y. Acad, Sci., 967: 500-05 (2002).
Maize, J. C., "Panniculitis," Cutaneous Pathology, Chapter 13: 327-344 (1998).
Malcom, G. et al. "Fatty Acid Composition of Adipose Tissue in Humans: Differences between Subcutaneous Sites," Am. J. Clin. Nutr., 60: 725-29 (1994).
Moschella, S. L. et al. "Diseases of the Subcutaneous Tissue," Derm., Section 2: 1169-1181 (1985).
Murphy, J. V. et al. "Frostbite: Pathogensesis and Treatment," The Journal of Trauma: Injury, Infection and Critical Care, 48(1): 171-178 (2000).
Phinney, S. D. et al. "Human Subcutaneous Adipose Tissue Shows Site Specific Differences in Fatty Acid Composition," Am. J. Clin. Nurt., 60: 725-29 (1994).
Renold, A. E. "Adipose Tissue," Handbook of Physiology, Chapter 15: 170-76, (1965).
Young, H. E. et al. "Isolation of Enbryonic Chick Myosatellite and Pluripotent Stem Cells," J. Tiss. Cult. Meth., 14: 85-92 (1992).
Communication, European Patent Application No. 05 854 660 (Sep. 1, 2008).
International Search Report, International Application No. PCT/US2005/045988 (Apr. 25, 2006).
Official Action, Japanese Patent Application No. 2007-547008 (Sep. 24, 2008).
Examination Report, United Kingdom Patent Application No. GB052638.3 (Sep. 25, 2008).
Requisition, Canadian Patent Application No. 2,478,887 (Dec. 23, 2008).
Final Rejection, Japanese Patent Application No. 2007-547008 (Feb. 3, 2009).
Search Report and Written Opinion, Singapore Patent Application No. 200704450-6 (Apr. 9, 2009).
Levchenko et al. "[Effect of dehydration on lipid metabolism]." WMJ Jan.-Feb. 1978;50(1):95-7.
L'Vova "[Lipid levels and lipid peroxidation in frog tissues during hyperthermia and hibernation]." WMJ Jan.-Feb. 1990;62(1):65-70.
Kuroda et al. "Thermal distribution of radio-frequency inductive hyperthermia using an inductive aperture-type applicator: evaluation of the effect of tumour size and depth." Med Biol Eng Comput May 1999;37(3):285-90.
Kundu et al. "Breath acetone analyzer: diagnostic tool to monitor dietary fat loss." Clin Chem Jan. 1993;39(1):87-92.
Kundu et al. "Novel solid-phase assay of ketone bodies in urine." Clin Chem Sep. 1991;37(9):1565-9.
Hale et al. "Influence of chronic heat exposure and prolonged food deprivation on excretion of magnesium, phosphorus, calcium, hydrogen ion & ketones." Aerosp Med Sep. 1968;39(9):919-26.
Bohm et al. "Saline-enhanced radiofrequency ablation of breast tissue: an in vitro feasibility study." Invest Radiol Mar. 2000;35(3):149-57.
Henry et al. 1999 Rev Med Liege 54(11): 864-866 (Abstract translation).
Donski et al. "The Effects of Cooling no Experimental Free Flap Survival." Brit J Plas Surg (1980) 33: 353-360.
Nielsen "Thermoregulation in Rest and Exercise." Acta Phys Scan Supp 323 (1969): 6-74.
Examiner's First Report, Australian Patent Application No. 2003220311 (Apr. 16, 2007).

(56) References Cited

OTHER PUBLICATIONS

Requisition, Canadian Patent Application No. 2,478,887 (Dec. 22, 2009).
Requisition, Canadian Patent Application No. 2,590,567 (Apr. 30, 2009).
Requisition, Canadian Patent Application No. 2,590,567 (Oct. 15, 2009).
First Office Action, Chinese Patent Application No. 038109387 (Mar. 2, 2007).
Notice of Re-examination, Chinese Patent Application No. 038109387 (Nov. 16, 2009).
Rejection Decision, Chinese Patent Application No. 03810938.7 (Feb. 27, 2009).
Notice of Re-examination Decision, Chinese Patent Application No. 03810938.7 (Jun. 23, 2010).
First Office Action, Chinese Patent Application No. 20050048173.X (Jan. 23, 2009).
Second Office Action, Chinese Patent Application No. 20050048173.X (Jul. 10, 2009).
Rejection Decision, Chinese Patent Application No. 20050048173.X (Dec. 25, 2009).
Communication, European Patent Application No. 03 716 609.7 (Apr. 19, 2006).
Summons to attend oral proceedings, European Patent Application No. 03 716 609.7 (Jun. 12, 2007).
Supplementary Partial European Search Report, European Patent Application No. 03 716 609 (Nov. 11, 2005).
Communication, European Patent Application No. 05 854 660.7 (Nov. 27, 2007).
Communication, European Patent Application No. 05 854 660.7-2319 (Mar. 11, 2010).
Summons to Attend Oral Heading, European Patent Application No. 07 117 532.7 (Apr. 15, 2010).
Communication, European Patent Application No. 07 117 532.7 (Jul. 10, 2009).
Communication, European Patent Application No. 07 117 532.7 (Sep. 9, 2008).
Communication, European Patent Application No. 07 117 532.7 (Apr. 3, 2008).
Examination Report, Great Britain Patent Application 0525638.3 (Jul. 14, 2009).
Notice Regarding Deficiencies, Israeli Patent Application No. 164115 (Aug. 4, 2008).
Notice of Deficiencies, Israeli Patent Application No. 164115 (Sep. 16, 2009).
Office Action, Japanese Patent Application No. 2003-576590 (Aug. 5, 2008).
Office Action, Japanese Patent Application No. 2003-576590 (Apr. 7, 2009).
Office Action, Japanese Patent Application 2003-576590 (Dec. 17, 2009).
International Preliminary Examination Report, International Application No. PCT1US03108014 (Mar. 29, 2004).
International Search Report, International Application No. PCT/US03/08014 (Sep. 23, 2003).
International Preliminary Report on Patentability, International Application No. PCT/US2005/045988 (Jun. 19, 2007).
Written Opinion, International Application No. PCT/US2005/045988 (Jun. 19, 2007).
Written Opinion, Brazilian Patent Application No. PI0308642-9 (May 25, 2012).
Examiner's First Report, Australian Patent Application No. 2005316277, (Mar. 11, 2010).
Examiner's First Report, Australian Patent Application No. 2009200451, (Feb. 16, 2011).
Written Opinion, Brazilian Patent Application No. PI0308642-9 (Mar. 15, 2013).
Requisition, Canadian Patent Application No. 2,590,567 (Dec. 23, 2008).
Requisition, Canadian Patent Application No. 2,478,887 (Mar. 29, 2011).
Requisition, Canadian Patent Application No. 2,478,887 (Mar. 8, 2012).
First Office Action, Chinese Patent Application No. 038109387 (Jan. 9, 2007).
Second Office Action, Chinese Patent Application No. 038109387 (Nov. 7, 2008).
Rejection Decision, Chinese Patent Application No. 038109387 (Feb. 27, 2009).
Notification of Re-Examination Decision, Chinese Patent Application No. 038109387 (Jun. 23, 2010).
Third Office Action, Chinese Patent Application No. 200910146673.7 (Apr. 25, 2013).
First Office Action, German Patent Application No. 10 2005 060 387.4-35 (Jan. 26, 2007).
Communication, European Patent Application No. 03716609, (Nov. 11, 2005).
Minutes of the oral proceedings, European Patent Application No. 07117532.7 (Aug. 9, 2010).
Communication, European Patent Application No. 101677565, (Aug. 31, 2010).
Communication, European Patent Application No. 101677565, (Oct. 25, 2010).
Communication, European Patent Application No. 101677565 (Jul. 4, 2011).
Summons to attend oral proceedings, European Patent Application No. 101677565 (Dec. 29, 2011).
Communication, European Patent Application No. 101816973 (Sep. 19, 2012).
Result of consultation, European Patent Application No. 101677565 (Mar. 19, 2012).
Result of consultation, European Patent Application No. 101677565 (Mar. 26, 2012).
Provision of a copy of the minutes, European Patent Application No. 101677565 (Apr. 10, 2012).
First Examination Report for Indian Patent Application No. 2607/CHENP/2007 (Aug. 1, 2011).
Hearing Notice for Indian Patent Application No. 2607/CHENP/2007 (Jun. 12, 2013).
Official Action, Japanese Patent Application No. 2008-182599 (Dec. 21, 2010).
Official Action, Japanese Patent Application No. 2008-182599 (Jun. 28, 2011).
Office Action, Korean Patent Application No. 10-2011-7002259 (Mar. 22, 2011).
Notice of Final Rejection, Korean Patent Application No. 10-2011-7002259 (Mar. 26, 2012).
Notice Requesting Submission of Opinion, Korean Patent Application No. 10-2007-7015553 (Jun. 24, 2010).
Notice of Decision of Final Rejection, Korean Patent Application No. 10-2007-7015553 (Dec. 28, 2010).
Decision of Final Rejection, Korean Patent Application No. 10-2007-7015553 (Jun. 28, 2012).
Office Action, Korean Patent Application No. 10-2011-7022066 (Jan. 16, 2012).
Official Action, Mexican Patent Application No. MX/a/2007/007208 (Apr. 8, 2009).
Invitation to Respond to Written Opinion, Singapore Patent Application No. 200704450-6 (Apr. 9, 2009).
Examination Report, Great Britian Patent Application No. GB0525638.3 (Apr. 8, 2009).
Examination Report, Great Britian Patent Application No. GB0525638.3 (Jul. 14, 2009).
Office Action, U.S. Appl. No. 11/016,196 (Apr. 22, 2008).
Office Action, U.S. Appl. No. 11/016,196 (Sep. 25, 2009).
Office Action, U.S. Appl. No. 11/016,196 (Mar. 23, 2010).
Office Action, U.S. Appl. No. 10/391,221 (Jul. 22, 2005).
Office Action, U.S. Appl. No. 10/391,221 (Jan. 25, 2006).
Office Action, U.S. Appl. No. 10/391,221 (Aug. 24, 2006).
Office Action, U.S. Appl. No. 10/391,221 (May 30, 2007).
Office Action, U.S. Appl. No. 13/895,923 (Aug. 30, 2013).
Office Action, U.S. Appl. No. 13/896,285 (Sep. 5, 2013).

(56) References Cited

OTHER PUBLICATIONS

Office Action, U.S. Appl. No. 13/896,287 (Aug. 30, 2013).
Office Action, U.S. Appl. No. 13/896,291 (Sep. 5, 2013).
Office Action, U.S. Appl. No. 13/896,637 (Sep. 13, 2013).
Hong et al., "Patterns of Ice Formation in Normal and Malignant Breast Tissue," Cryobiology, 31:109-120 (1994).
Schoning, at al. "Experimental Frostbite: Freezing Times, Rewarming Times, and Lowest Temperatures of Pig Skin Exposed to Chilled Air." Cryobiology 27, 189-193 (1990), pp. 189-193.
Invalidity Excerpts from Clinipro Technical Report for Spanish Patent ES 2 359 581 T3 (May 18, 2012).
Judgment No. 13/2013, *The General Hospital Corporation & Zeltiq Aesthetics Inc.* v. *Clinipro S.L. & Aquaestetica Consultores S.L.*, Commercial Court No. 5 of Barcelona (Jan. 25, 2013).
Opinion on Validity of the Patent EP1490005B1 (Validated in Spain as ES2300569T3) and EP1917935B1 (Validated in Spain as ES2359581) (Sep. 6, 2012).
Oppositional Document for Clinipro, S.L., Mercentile Court No. 5 of Barcelon (Mar. 22, 2013).
Pleading on behalf of Macé and Clinipro against the General Hospital Corporation and Zeltiq Aesthetics Inc., Docket No. 11/18480 (May 7, 2012).
Pleading No. 2 on behalf of Macé and Clinipro Against the General Hospital Corporation and Zeltiz Aesthetics Inc., Docket No. 11/18480 (Dec. 18, 2012).
Pleading No. 3 on behalf of Mr. Patrick Macé and Clinipro against the General Hospital Corporation and Zeltiq Aesthetics Inc., Docket No. 11/18480 (Mar. 19, 2013).
Judgment, *The General Hospital Corporation* v. *Mace, Tribunal de Grande Instance de Paris*, Docket No. 11/18480 (May 23, 2013).
Pleading, *Macé v. The General Hospital Corporation*, Division 5—Chamber 1, Docket No. 13/13050 (Sep. 26, 2013).
Authorized Statement of Defence of B&B Groups S.R.L. against New Technology Research Medical Equipment s.r.l. And against Zeltiq Aesthetics Inc., Court of Milan, Business Division, Docket No. 41207/2012 (Mar. 25, 2013).
Judgment No. 169/2014, Barcelona Provincial Court (May 13, 2014).
Complaint, *Zeltiq Aesthetics, Inc.* v. *Fischer*, District Court Munich—Patent Litigation Court (May 27, 2014).
Patent Examination Report No., Australian Patent Application No. 2012204124 (Nov. 29, 2013).
Rejection Decision, Chinese Patent Application No. 200910146673.7 (Oct. 29, 2013).
Notification of Reexamination, Chinese Patent Application No. 200910146673.7 (Jun. 27, 2014).
Communication, European Patent Application No. 10 181 697.3 (Jan. 15, 2014).
Communication, European Patent Application Serial No. 10 181 697.3 (Jan. 30, 2014).
Office Action, U.S. Appl. No. 11/016,196 (Oct. 25, 2013).
Office Action, U.S. Appl. No. 13/896,285 (Mar. 27, 2014).
Office Action, U.S. Appl. No. 13/896,287 (Apr. 10, 2014).
Office Action, U.S. Appl. No. 13/896,291 (Mar. 6, 2014).
Office Action, U.S. Appl. No. 13/896,637 (Apr. 23, 2014).
3rd Pleading, on behalf of Mr. Patrick Mace and Clinipro against The General Hospital Corporation and Zeltiq Aesthetics Inc., (Sep. 25, 2014).
Laurent Charras, Analysis Regarding the Sufficiency of the Description for Patent No. EP 1490005 (Sep. 24, 2014).
H. Ray Jalian & Mathew M. Avram, "Cryolipolysis: A Historical Perspective and Current Clinical Practice," 32(1) Semin. Cutan. Med. Surg. 31-34 (2013).
Dieter Manstein et al., "Selective Cryolysis: A Novel Method of Non-Invasive Fat Removal," 40 Lasers in Surgery & Medicine 595-604 (2008).
Hernán Pinto et al., "Study for the evaluation of the efficacy of Lipocryolysis (EEEL)" (Nov. 30, 2011).
Hernán R. Pinto, "A Study to Evaluate the Action of Lipocryolysis," 33(3) CryoLetters 176-80 (2012).
Brian Zelickson et al., "Cryolipolysis for Noninvasive Fat Cell Destruction: Initial Results from a Pig Model," 35 Dermatol. Surg. 1-9 (2009).
Summons to Attend Oral Proceedings Pursuant to Rule 115(1) EPC, EP Application No. 10181697.3, Jul. 28, 2015.
Communication Pursuant to Rule 114(2), EPC, EP Application No. 10181697.3, Feb. 25, 2015.
French Republic Cour D'Appel de Paris, Decision of Jan. 12, 2016, *Mace trading as Clinipro et al.* v. *The General Hospital Corporation et al.* (Jan. 12, 2016).
Office Action, U.S. Appl. No. 13/896,285 (Dec. 30, 2015).
Office Action, U.S. Appl. No. 13/896,287 (Dec. 31, 2015).
Office Action, U.S. Appl. No. 13/896,637 (Jan. 13, 2016).

* cited by examiner

METHODS AND DEVICES FOR SELECTIVE DISRUPTION OF FATTY TISSUE BY CONTROLLED COOLING

RELATED APPLICATIONS/PATENTS & INCORPORATION BY REFERENCE

This application is a division of U.S. application Ser. No. 10/391,221, now U.S. Pat. No. 7,367,341 claiming priority to U.S. application Ser. No. 60/365,662, filed on Mar. 15, 2002, the contents of which are herein expressly incorporated by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself, and, each of these documents or references ("herein-cited references"), as well as each document or reference cited in each of the herein-cited references (including any manufacturer's specifications, instructions, etc.), is hereby expressly incorporated herein by reference.

STATEMENT OF RIGHTS TO INVENTIONS MADE UNDER FEDERALLY SPONSORED RESEARCH

Not applicable.

FIELD OF THE INVENTION

The present invention relates to methods for use in the selective disruption of lipid-rich cells by controlled cooling. The present invention further relates to a device for use in carrying out the methods for selective disruption of lipid-rich cells by controlled cooling. Other aspects of the invention are described in or are obvious from the following disclosure (and within the ambit of the invention).

BACKGROUND

The subcutaneous fatty tissue of newborns is unusually sensitive to the cold. In newborns, the intracellular lipid content of the subcutaneous fat cells, or "adipocytes," comprises increased ratios of highly saturated triglycerides. Even moderately cold temperatures can adversely affect cells having a highly saturated lipid content, rendering newborn subcutaneous fatty tissue vulnerable to adipocyte necrosis following exposure to the cold. Hypothermia of subcutaneous fatty tissue can result in associated inflammation of the dermis and/or epidermis. For example, disorders of cold panniculitis in newborns are known to produce painful skin lesions.

As newborns mature, the ratio of saturated to unsaturated fatty acids among intracellular triglycerides of adipocytes gradually decreases. Having a higher content of unsaturated fatty acids is more protective against the cold, and the occurrence of cold panniculitis in infants gradually subsides. For detailed reviews on the subject of cold panniculitis, see Epstein et al. (1970) New England J. of Med. 282(17):966-67; Duncan et al. (1966) Arch. Derm. 94:722-724; Kellum et al. (1968) Arch. Derm. 97:372-380; Moschella, Samuel L. and Hurley, Harry J. (1985) Diseases of the Corium and Subcutaneous Tissue. In Dermatology (W.B. Saunders Company): 1169-1181; John C Maize (1998) Panniculitis In Cutaneous Pathology (Churchill Livingstone): 327-344; Bondei, Edward E. and Lazarus, Gerald S. (1993) Disorders of Subcutaneous Fat (Cold Panniculitis). In Dermatology in General Medicine (McGraw-Hill, Inc.): 1333-1334

In adults, the intracellular lipid content varies among cell types. Dermal and epidermal cells, for instance, are relatively low in unsaturated fatty acids compared to the underlying adipocytes that form the subcutaneous fatty tissue. For a detailed review of the composition of fatty tissue in mammals, see Renold, Albert E. and Cahill, Jr., George F. (1965) Adipose Tissue. In Handbook of Physiology (American Physiology Society): 170-176. As a result, the different cell types, e.g., lipid-rich and non-lipid-rich cells, have varying degrees of susceptibility to the cold. In general, non-lipid-rich cells can withstand colder temperatures than lipid-rich cells.

It would be highly desirable to selectively and non-invasively damage adipocytes of the subcutaneous fatty tissue without causing injury to the surrounding dermal and epidermal tissue. Both health and cosmetic benefits are known to result from reduction of fatty tissue, however, current methods, such as liposuction, involve invasive procedures with potentially life threatening risks (e.g., excessive bleeding, pain, septic shock, infection and swelling).

Current methods for non-invasive removal of subcutaneous fatty tissue include the use of radiant energy and cooling solutions. U.S. Pat. Nos. 5,143,063, 5,507,790 and 5,769,879 describe methods for using radiant energy to reduce subcutaneous fatty tissue, however, the applied energy levels are difficult to control and often there is collateral damage to the dermis and/or epidermis. Cooling solutions proposed by WO 00/44346 do not stabilize skin surface temperatures and therefore, also fail to adequately protect against collateral damage to the dermis and/or epidermis.

A previous study conducted in Guinea Pigs described the removal of subcutaneous fatty tissue by cryo-damage. Burge, S. and Dawber, R. (1990) Cryobiology 27:153-163. However this result was achieved using relatively aggressive cooling modalities (e.g., liquid nitrogen), which induced epidermal damage. Ideally, removal of subcutaneous fatty tissue by cooling would not cause associated damage to the epidermis.

Temperature controlled methods and devices for selectively damaging lipid-rich cells (e.g., adipocytes comprising the subcutaneous fatty tissue) without causing injury to non lipid-rich cells (e.g., dermis and/or epidermis) were heretofore unknown.

SUMMARY

It has now been shown that adipose tissue comprising lipid-rich cells can be selectively disrupted without causing injury to the surrounding non lipid-rich tissue (e.g., dermal and epidermal tissue) by controlling the temperature and/or pressure applied to the respective tissues.

In one aspect, the invention relates to a cooling method for selective disruption of lipid-rich cells in a non-infant human subject comprising applying a cooling element proximal to the subject's skin to create a temperature gradient within a local region sufficient to selectively disrupt and thereby reduce the lipid-rich cells of said region, and, concurrently therewith maintain the subject's skin at a temperature wherein non lipid-rich cells proximate to the cooling element are not disrupted.

In one embodiment, the invention relates to a method for treating a region of a subject's body to achieve a desired reduction in subcutaneous adipose tissue, comprising a) applying a cooling element proximal to the subject's skin in the region where subcutaneous adipose tissue reduction is desired to create a temperature gradient within said region sufficient to selectively disrupt lipid-rich cells therein, and, simultaneously therewith maintain the subject's skin at a temperature wherein non lipid-rich cells proximate to the cooling element are not disrupted; b) repeating the application of the cooling element to the subject's skin of step (a) a plurality of times until the desired reduction in subcutaneous adipose tissue has been achieved.

In another aspect, the invention relates to a device for selectively disrupting lipid-rich cells in a non-infant human subject by cooling comprising: means for creating a temperature gradient within a local region of the subject's skin to selectively disrupt and thereby reduce lipid-rich cells of the region, while, concurrently therewith, maintaining the subject's skin at a temperature whereby non lipid-rich cells are not disrupted.

In one embodiment, the invention relates to an apparatus for locally reducing lipid-rich cells, comprising a treatment device operable to receive a cooling agent; a cooling agent source connected to the treatment device for supplying said cooling agent; a control unit coupled to the treatment device and the cooling agent source for controlling a cooling temperature of said cooling agent, wherein said treatment device exposes target tissue to said cooling agent, which selectively induces damage to lipid-rich cells at said target tissue.

In another embodiment, the invention further relates to an apparatus for locally reducing lipid-rich cells, comprising a means for setting a cooling agent to a predetermined temperature; and a means for applying said cooling agent to target tissue, whereby the cooling agent selectively induces damage to lipid-rich cells at said target tissue.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

These and other objects and embodiments are described in or are obvious from and within the scope of the invention, from the following Detailed Description.

DESCRIPTION OF THE DRAWINGS

FIG. 7 depicts histology of the subcutaneous adipose tissue 17 days after cold exposure (Pig II, Site E).

DETAILED DESCRIPTION

Figure 1A:
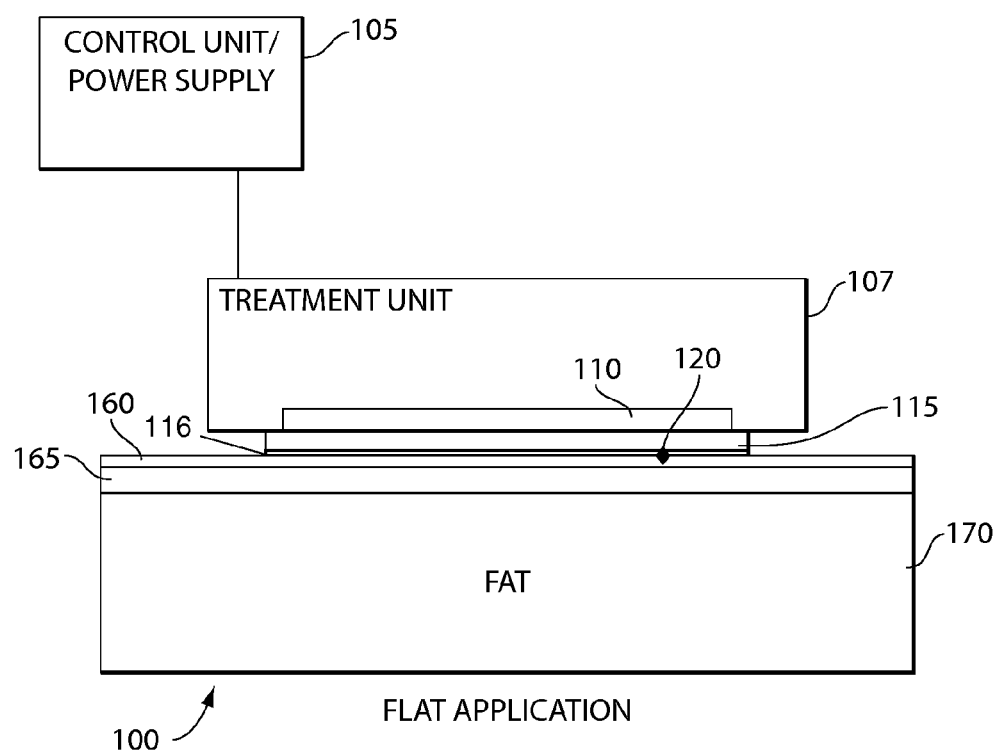
FIG. 1A illustrates a treatment system.

The present invention relates to a method for locally reducing adipose tissue comprising applying a cooling element to a subject at a temperature sufficient to selectively disrupt lipid-rich cells, wherein the temperature does not produce unwanted effects in non lipid-rich cells. Preferably, the cooling element is coupled to or contains a cooling agent.

In one aspect, the invention relates to a cooling method for selective disruption of lipid-rich cells in a non-infant human subject comprising applying a cooling element proximal to the subject's skin to create a temperature gradient within a local region sufficient to selectively disrupt and thereby reduce the lipid-rich cells of said region, and, concurrently therewith maintain the subject's skin at a temperature wherein non lipid-rich cells proximate to the cooling element are not disrupted.

In one embodiment, the invention relates to a method for treating a region of a subject's body to achieve a desired reduction in subcutaneous adipose tissue, comprising a) applying a cooling element proximal to the subject's skin in the region where subcutaneous adipose tissue reduction is desired to create a temperature gradient within said region sufficient to selectively disrupt lipid-rich cells therein, and, simultaneously therewith maintain the subject's skin at a temperature wherein non lipid-rich cells proximate to the cooling element are not disrupted; b) repeating the application of the cooling element to the subject's skin of step (a) a plurality of times until the desired reduction in subcutaneous adipose tissue has been achieved.

Cooling elements of the present invention can contain cooling agents in the form of a solid, liquid or gas. Solid cooling agents can comprise, for example thermal conductive materials, such as metals, metal plates, glasses, gels and ice or ice slurries. Liquid cooling agents can comprise, for example, saline, glycerol, alcohol, or water/alcohol mixtures. Where the cooling element includes a circulating cooling agent, preferably the temperature of the cooling agent is constant. Salts can be combined with liquid mixtures to obtain desired temperatures. Gasses can include, for example, cold air or liquid nitrogen.

In one embodiment, cooling elements can be applied such that direct contact is made with a subject, via either the agent or the element. In another embodiment, direct contact is made via the agent alone. In yet another embodiment, no direct contact is made via either the agent or the element; cooling is a carried out by proximal positioning of the cooling element and/or agent.

Preferably, the temperature of the cooling agent is less than about 37° C., but not less than −196° C. (i.e, the temperature of liquid nitrogen).

Preferably, the temperature range of the administered cooling element is between about 40° C. and −15° C., even more preferably between 4° C. and −10° C. if the cooling agent is a liquid or a solid. Generally, the cooling element is preferably maintained at an average temperature of between about −15° C. and about 35° C., 30° C., 25° C., 20° C., 15° C., 10° C., or 5° C.; about −10° C. and about 35° C., 30° C., 25° C., 20° C., 15° C., 10° C., or 5° C.; about −15° C. and about 20° C., 15° C., 10° C., or 5° C.

The cooling element and/or agent can be applied for up to two hours. Preferably, the cooling element is applied for between 1 to 30 minutes. The cooling element can be applied for at least one hundred milliseconds (e.g., shorter durations are envisioned, for instance, with sprays). For example, liquid nitrogen can be applied in very short intervals (e.g., about 1 second), repeatedly (e.g., about 10-100 times) and between applications, a temperature that does not cause epidermal damage is maintained (e.g., about 0° C. to −10° C., depending on the length of exposure). In a gentle cooling regime, for example, the liquid nitrogen can be sprayed from a distance (e.g., from about 10 to 30 cm) wherein some portion of the liquid nitrogen droplets evaporate during the spraying and/or mix with ambient air.

Cooling elements and/or agents of the present invention are applied, for example, to the skin surface through either direct or indirect contact. A subject's skin comprises the epidermis, dermis or a combination thereof. The cooling element and/or agent is a non-toxic cooling agent when applied directly to the skin surface.

The cooling element and/or agent can be applied more than once, for example, in repetitious cycles. The cooling agent can be applied in a pulsed or continuous manner. The cooling element and/or agent can be applied by all conventional methods known in the art, including topical application by spray if in liquid form, gas or particulate solid material. Preferably, application is by external means, however, cooling elements and/or agents of the present invention can also be applied subcutaneously by injection or other conventional means. For example, the cooling agent can be applied directly to the subcutaneous tissue and then either removed after contact or left in the subcutaneous tissue to achieve thermal equilibration and therefore cooling of the lipid-rich tissue (e.g., subcutaneous injection of a liquid cooling agent or of small cooling particles, such as pellets or microbeads).

Preferably, methods of the present invention are non-invasive (e.g., superficial, laparoscopic or topical procedures not requiring invasive surgical techniques).

The cooling element and/or agent can be applied to one defined area or multiple areas. Spatial distribution of the cooling element and/or agent can be controlled as needed. Generally, the dimension of the surface area (e.g., where the cooling agent is in contact with the skin) should be at least three times the depth of subcutaneous fatty tissue that is targeted for cooling. Preferably, the minimum diameter of the surface area is at least 1 cm$^2$. Even more preferably, the diameter of the surface area is between 3 to 20 cm$^2$. Determination of the optimal surface area will require routine variation of several parameters. For example, larger surface areas, such as those over 3500 cm$^2$, can be cooled according to the methods of the present invention if hypothermia is prevented by additional means. Hypothermia can be prevented by compensating for the heat transfer away from the body at other sites (e.g., applying warm water at one or more additional sites). Multiple cooling elements and/or agents can be employed, for example, in contacting larger surface areas (e.g., greater than 3500 cm$^2$).

The cooling element and/or agent can follow the contour of the area to which it is applied. For example, a flexible apparatus can be used to follow the contour of the surface area where cooling is applied. The apparatus can also modify the shape of the contacted surface such that the surface is contoured around or within the cooling agent or the apparatus containing the cooling agent upon contact. The cooling element and/or agent can contact more than one surface at once, for example, when the surface is folded and contacted on either side by the cooling element and/or agent. Preferably, a skin fold is contacted on both sides by the cooling element and/or agent to increase the efficiency of cooling.

Preferably, the solid cooling element and/or agent is shaped to enhance thermodynamic heat exchange ("thermal exchange") at the contacted surface (e.g., skin surface). In order to enhance conduction, a liquid can be used at the interface between the solid cooling agent and the contacted surface.

Where necessary, application of the cooling element and/or agent can be coupled with use of a pain management agent, such as an anesthetic or analgesic (cooling alone has analgesic properties, thus use of additional pain management agents is optional). Local anesthetics, for example, can be topically applied at the point of contact either before, after or during application of the cooling agent. Where necessary, systemic administration of the anesthetic can be provided through conventional methods, such as injection or oral administration. The temperature of the cooling agent can be changed during the treatment, for example, so that the cooling rate is decreased in order to provide a treatment causing less discomfort. In addition, methods of the present invention can be performed in combination with other fat reduction procedures known in the art, such as liposuction.

Preferably, lipid-rich cells of the present invention are adipocytes within subcutaneous fatty tissue or cellulite. Thus, lipid-rich cells comprising the subcutaneous adipose tissue are targeted for disruption by methods of the present invention. In addition, it is within the ambit of the invention to target disruption of lipid-rich cells comprising adventicia surrounding organs or other internal anatomical structures.

The intracellular lipids of adipocytes are confined within the paraplasmatic vacuole. There are univacular and plurivacular adipocytes within the subcutaneous fatty tissue. Most are univacular, and greater than about 100 um in diameter. This size can increase dramatically in obese subjects due to an increase in intracellular lipid content.

Preferably, lipid-rich cells of the present invention have a total intracellular lipid content of between 20-99%. Preferably, lipid-rich cells of the present invention have an intracellular lipid content comprised of about 20-50% saturated triglycerides, and even more preferably about 30-40% saturated triglycerides. Intracellular triglycerides include, but are not limited to, saturated fatty acids e.g., myristic, palmitic and stearic acid; monounsaturated fatty acids, e.g., palmitoleic and oleic acid; and polyunsaturated fatty acids e.g., linoleic and linolenic acid.

Preferably, lipid-rich cells of the present invention are located within subcutaneous adipose tissue. The saturated fatty acid composition of subcutaneous adipose tissue varies at different anatomical positions in the human body. For example, human subcutaneous adipose tissue in the abdomen can have the following composition of saturated fatty acids: myristic (2.6%), palmitic (23.8%), palmitoleic (4.9%), stearic (6.5%), oleic (45.6%), linoleic (15.4%) and linolenic acid (0.6%). The subcutaneous adipose tissue of the abdominal area can comprise about 35% saturated fatty acids. This is comparatively higher than the buttock area, which can comprise about 32% saturated fatty acids. At room temperature, saturated fatty acids of the abdominal area are in a semisolid state as a result of the higher fatty acid content. The buttock area is not similarly affected. Malcom G. et al., (1989) Am. J. Clin. Nutr. 50(2):288-91. One skilled in the art can modify temperature ranges or application times as necessary to account for anatomical differences in the response to cooling methods of the present invention.

Preferably, non lipid-rich cells of the present invention have a total intracellular lipid content of less than 20%, and/or are not disrupted by cooling methods of the present invention. Preferably, non lipid-rich cells of the present invention include cells having an intracellular lipid content comprising less than about 20% highly saturated triglycerides, even more preferably less than about 7-10% highly saturated triglycerides. Non lipid-rich cells include, but are not limited to, those surrounding the subcutaneous fatty tissue, such as cells of the vasculature, peripheral nervous system, epidermis (e.g., melanocytes) and dermis (e.g., fibrocytes).

Damage to the dermis and/or epidermis that is avoided by the methods of the present invention can involve, for example, inflammation, irritation, swelling, formation of lesions and hyper or hypopigmentation of melanocytes.

Without being bound by theory, it is believed that selective disruption of lipid-rich cells results from localized crystalization of highly saturated fatty acids upon cooling at temperatures that do not induce crystalization of highly saturated fatty acids in non lipid-rich cells. The crystals rupture the bilayer membrane of lipid-rich cells, causing necrosis. Thus, damage of non lipid-rich cells, such as dermal cells, is avoided at temperatures that induce crystal formation in lipid-rich cells. It is also believed that cooling induces lipolysis (e.g., metabolism) of lipid-rich cells, further enhancing the reduction in subcutaneous adipose tissue. Lipolysis may be enhanced by local cold exposure inducing stimulation of the sympathetic nervous system.

In one embodiment, the temperature of the lipid-rich cells is not less than about −10° C. Preferably, the temperature of the lipid-rich cells is between −10° C. and 37° C. More preferably, the temperature of the lipid-rich cells is between −4° C. and 20° C. Even more preferably, the temperature of the lipid-rich cells is between −2° C. and 15° C. Preferably, the lipid-rich cells are cooled to less than 37° C., for up to two hours. Generally, the lipid-rich cells are preferably maintained at an average temperature of between about −10° C. and about 37° C., 35, 30° C., 25° C., 20° C., 15° C., 10° C., or 4° C.; about −4° C. and about 35° C., 30° C., 25° C., 20° C., 15° C., 10° C., or 4° C.; about −2° C. and about 35, 30° C., 25° C., 20° C., 15° C., 10° C., or 5° C.

In yet another embodiment, the temperature range of the lipid-rich cells oscillates between 37° C. and −10° C. Methods of pulse cooling followed by brief periods of warming can be used to minimize collateral damage to non lipid-rich cells. More preferably, the temperature range of the lipid-rich cells oscillates between −8° C. and 33° C. Even more preferably, the temperature range of the lipid-rich cells oscillates between −2° C. and 15° C. The temporal profile of the cooling of the skin can be performed in one continuous cooling act or in multiple cooling cycles or actually a combination of cooling with active heating cycles.

Cooling methods of the present invention advantageously eliminate unwanted effects in the epidermis. In one embodiment, the temperature of the epidermis is not less than about −15° C. Preferably, the temperature of the epidermis is between about −10° C. and 35° C. More preferably, the temperature of the epidermis is between about −5° C. and 10° C. Even more preferably, the temperature of the epidermis is between about −5° C. and 5° C.

Cooling methods of the present invention advantageously eliminate unwanted effects in the dermis. In one embodiment, the temperature of the dermis is not less than about −15° C. Preferably, the temperature of the dermis is between about −10° C. and 20° C. More preferably, the temperature of the dermis is between about −8° C. and 15° C. Even more preferably, the temperature of the dermis is between about −5° C. and 10° C. In a preferred embodiment, the lipid-rich cells are cooled to about −5° C. to 5° C. for up to two hours and the dermal and epidermal cells maintain an average temperature of about 0° C. In a most preferred embodiment, the lipid-rich cells are cooled to about −5 to 15° C. for times ranging from about a minute, up to about two hours.

Methods of the present invention can be applied in short intervals (e.g., 1 minute, 5 minute, 15 minute, 30 minute and 60 minute time intervals) or long intervals (e.g., 12 hour and 24 hour time intervals). Preferably intervals are between 5 and 20 minutes. Heat can optionally be applied between intervals of cooling.

Feedback mechanisms can be employed to monitor and control temperatures in the skin (i.e., dermis, epidermis or a combination thereof) subcutaneous adipose tissue. A feedback mechanism can monitor the temperature of a subject's skin to ensure that the temperature therein in does not fall below a predetermined minimum temperature, for example, about −10° C. to about 30° C. A non-invasive device can be externally applied to measure surface temperature at the point of contact and/or the surrounding region. An invasive device, such as a thermocouple, can be used to measure internal temperatures.

Feedback mechanisms can include all known in the art to monitor temperature and/or crystal formation. Crystal formation can be measured, for example by ultrasound imaging and acoustical, optical, and mechanical measurements. Mechanical measurements can include, for example, measurements of tensile strength.

In one embodiment, a multilayer model can be employed to estimate temperature profiles over time and within different depths. Temperature profiles are designed to produce a temperature gradient within the tissue, having a lower temperature at the surface. In a preferred embodiment, temperature profiles are designed to minimize blood flow during cooling. Feedback mechanisms comprising, for example, thermocouples, ultrasound (e.g., to detect phase changes of the subcutaneous adipose tissue) or shock wave propagation (e.g., propagation of a shock wave is altered if a phase transition occurs) can be employed to achieve optimal temperature gradients.

Substantial cooling of the subcutaneous adipose layer, for example to a target temperature between about −5° C. and 15° C., by cooling at the skin surface has several requirements. Heat extracted from the skin surface establishes a temperature gradient within the skin, which in turn cools first the epidermis, dermis, and finally subcutaneous adipose layers. Dermal blood flow brings heat from the body core to the dermis. Dermal blood flow can therefore severely limit cooling of the deep dermis and subcutaneous adipose. Therefore, it is strongly preferred to temporarily limit or eliminate cutaneous blood flow, for example by locally applying a pressure to the skin greater than the systolic blood pressure, while cooling as a treatment to achieve reduction in subcutaneous adipose. A general requirement is that the time of cooling at the skin surface must be long enough to allow heat to flow from the dermis and subcutaneous adipose layers in order to achieve the desired temperature for treatment of the same. When the subcutaneous adipose is cooled to a temperature below that for crystallization of its lipids, the latent heat of freezing for these lipids must also be removed, by diffusion. The skin surface cooling temperature and cooling time can be adjusted to control depth of treatment, for example the anatomical depth to which subcutaneous adipose is affected. Heat diffusion is a passive process, and the body core temperature is nearly always close to 37° C. Therefore, another general requirement is that the skin surface temperature during cooling, must be lower than the desired target (e.g., adipocytes) temperature for treatment of the region, for at least part of the time during which cooling is performed.

When cooling a diameter of skin greater than about 2 cm, and with no blood flow, one-dimensional heat diffusion offers a good approximation for estimating temperature profiles in skin over time during cooling. Heat diffusion is governed by the general diffusion equation, $\delta T/\delta t = \kappa \delta^2 T/\delta z^2$, where T (z,t) is the temperature in skin as a function of depth z and time t, and $\kappa$ is the thermal diffusivity, which is approximately $1.3 \times 10^{-3}$ cm$^2$s$^{-1}$ for skin tissue. Solutions and approximate solutions to the heat diffusion equation have been made for planar geometry of a semi-infinite slab, approximating the situation for skin. When the surface of the skin (z=0) is held at a given lower temperature, a useful approximation is that heat flow from a depth z requires a time of approximately $t \cong z^2$ to achieve a temperature difference ½ of the initial difference, where t is in seconds and z is in millimeters. Thus, $z^2$ can be considered an approximate value for a thermal time constant. For example, if the initial skin temperature is 30 C, and ice at 0 C is placed firmly against the skin surface, it requires about 1 second for the temperature at a depth of 1 millimeter, to reach about 15 C. The subcutaneous fat layer typically begins at about z≅3 mm, and extends for millimeters up to many centimeters thick. The thermal time constant for heat transfer from the top of the subcutaneous adipose layer, is therefore about 10 seconds. To achieve substantial cooling of subcutaneous adipose, at least several and preferably greater than 10 thermal time constants of cooling time are required. Therefore, cooling must be maintained for about 30-100 seconds at the skin surface, and in the absence of dermal blood flow, for the temperature of the topmost portion of subcutaneous adipose to approach that of the cooled skin surface. The latent heat of crystallization for lipids, mentioned above, must also be removed when the fat temperature drops below that for crystallization. Therefore in general, cooling times over 1 minute are desired, and cooling times greater than about 1 minute can be used to adjust the depth of adipocytes affected, for times up to more than an hour.

Accordingly, in yet another embodiment, the dermis is cooled at a rate sufficient to induce vasoconstriction. Blood circulation within the dermis stabilizes the temperature of the dermis close to body temperature. In order to cool subcutaneous adipose tissue to temperatures below body temperature, blood flow can be minimized. Fast cooling of the epidermal surface can achieve refectory vasoconstriction that limits blood circulation in an appropriate way.

In yet another embodiment, a vasoconstrictive drug is administered to induce vasoconstriction. Vasoconstrictive drugs, for example, can be topically applied at the point of contact either before, after or during application of the cooling agent. Where necessary, systemic administration of the vasoconstrictive drug can be provided through conventional methods, such as injection or oral administration. The vasoconstrictive drug can be any known in the art. Preferably, the vasoconstrictive drug is EMLA cream or epinephrine.

In yet another embodiment, pressure is applied to a surface, either at the point of contact with the cooling agent or in proximity thereto, such that lateral blood flow is limited. Pressure can be applied, for example, to a skin surface by compressing the skin surface into a skin fold comprising single or multiple folds. Pressure can also be by applying a vacuum either at the point of contact with the cooling agent or in proximity thereto.

Without being bound by theory, it is believed that the rate of formation of crystals in lipid-rich cells can be altered by the application of pressure during the cooling process. Sudden crystallization, rather than a slow accumulation of crystals, would cause greater damage to the lipid-rich cells. It is also believed that the application of pressure can force the movement of the crystals within the lipid-rich cells, enhancing the damage to the bilayer membrane. Furthermore, different compartments of the subcutaneous adipose tissue have different viscosities. In general, the viscosity is enhanced at colder temperatures (e.g., those particularly close to the point of phase change). Because the phase change for lipid-rich cells occurs at higher temperatures than non lipid-rich cells, non-uniform tension lines form within the subcutaneous adipose tissue upon the application of pressure. It is believed that pronounced damage occurs within these tension lines.

In yet another aspect, the temperature of the dermis and/or epidermis oscillates between 35° C. and −15° C. More preferably, the temperature of the dermis and/or epidermis oscillates between −10° C. and 10° C. Even more preferably, the temperature of the dermis and/or epidermis oscillates between −8° C. and 8° C. Oscillating temperatures at the skin surface can provide intermittent warming to counteract potential side effects of the cooling process (e.g., crystal formation in the dermal or epidermal cells).

In yet another aspect, application of the cooling agent is coupled with the application of electric or acoustic fields, either constant or oscillating in time, localized in the dermis and/or epidermis to reduce or eliminate crystal formation therein.

FIG. 1A illustrates a treatment system 100 for cooling a target area in accordance with an embodiment of the invention. As shown in FIG. 1A, treatment system 100 may include a control unit 105 and a treatment unit 107, which may include a cooling/heating element 110 and a treatment interface 115.

Control unit 105 may include a power supply, for example, control unit may be coupled to a power source, for supplying power to treatment unit 107. Control unit 105 can also include a computing device having control hardware and/or software for controlling, based on inputted properties and/or parameters, cooling/heating element 110 and treatment interface 115. Treatment interface 115 can include a detector 120.

Figure 1B:
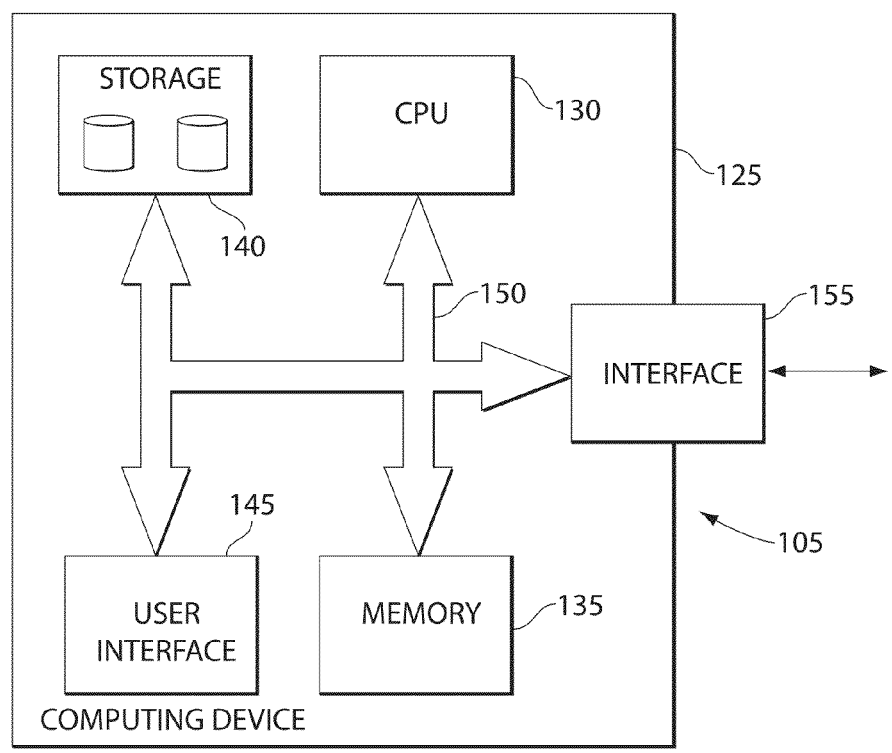
FIG. 1B depicts a diagram illustrating a configuration of control unit.

FIG. 1B is a diagram illustrating a configuration of control unit 105 in accordance with an embodiment of the invention. As shown in FIG. 1B, control unit 105 can comprise a computing device 125, which can be a general purpose computer (such as a PC), workstation, mainframe computer system, and so forth. Computing device 125 can include a processor device (or central processing unit "CPU") 130, a memory device 135, a storage device 140, a user interface 145, a system bus 150, and a communication interface 155. CPU 130 can be any type of processing device for carrying out instructions, processing data, and so forth. Memory device 135 can be any type of memory device including any one or more of random access memory ("RAM"), read-only memory ("ROM"), Flash memory, Electrically Erasable Programmable Read Only Memory ("EEPROM"), and so forth. Storage device 140 can be any data storage device for reading/writing from/to any removable and/or integrated optical, magnetic, and/or optical-magneto storage medium, and the like (e.g., a hard disk, a compact disc-read-only memory "CD-ROM", CD-ReWritable "CD-RW", Digital Versatile Disc-ROM "DVD-ROM", DVD-RW, and so forth). Storage device 140 can also include a controller/interface (not shown) for connecting to system bus 150. Thus, memory device 135 and storage device 140 are suitable for storing data as well as instructions for programmed processes for execution on CPU 130. User interface 145 may include a touch screen, control panel, keyboard, keypad, display or any other type of interface, which can be connected to system bus 150 through a corresponding input/output device interface/adapter (not shown). Communication interface 155 may be adapted to communicate with any type of external device, including treatment unit 107. Communication interface 155 may further be adapted to communicate with any system or network (not shown), such as one or more computing devices on a local area network ("LAN"), wide area network ("WAN"), the internet, and so forth. Interface 155 may be connected directly to system bus 150, or can be connected through a suitable interface (not shown). Control unit 105 can, thus, provide for executing processes, by itself and/or in cooperation with one or more additional devices, that may include algorithms for controlling treatment unit 107 in accordance with the present invention. Control unit 105 may be programmed or instructed to perform these processes according to any communication protocol, programming language on any platform. Thus, the processes may be embodied in data as well as instructions stored in memory device 135 and/or storage device 140 or received at interface 155 and/or user interface 145 for execution on CPU 130.

Referring back to FIG. 1A, treatment unit 107 may be a handheld device, an automated apparatus, and the like. Cooling/heating element 110 can include any type of cooling/heating component, such as a thermoelectric cooler and the like.

Figure 1C:
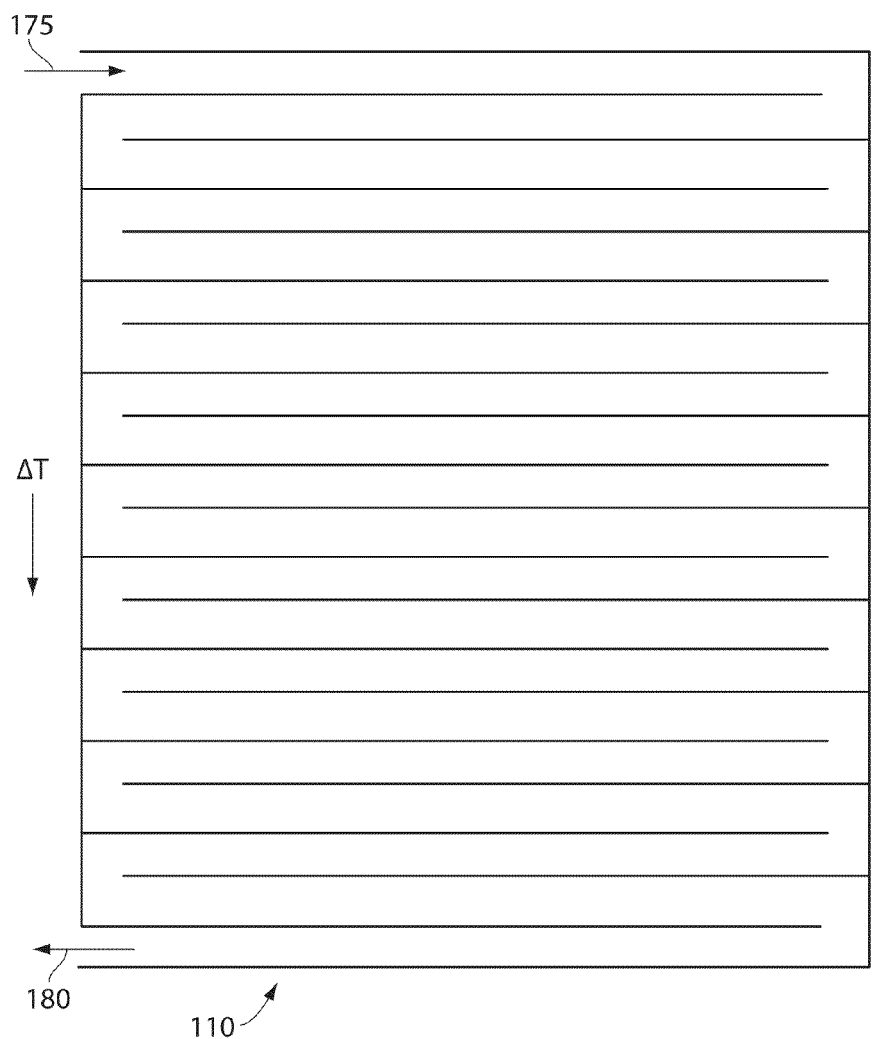
FIG. 1C depicts a diagram showing cooling/heating element.

FIG. 1C is a diagram showing cooling/heating element 110 in accordance with an embodiment with the present invention. As shown in FIG. 1C, cooling/heating element 110 can include a network of passages where a cooling/heating fluid flows through. The passages may be formed by any heat conducting tubing and the like. The cooling/heating fluid can be directed into element 110 through an input 175 and expelled through an output 180. The cooling/heating fluid may be any fluid having a controlled temperature, such as cooled air/gas or liquid. For example, a saltwater or acetone bath that is cooled using ice or frozen carbon dioxide may be used as a source of cooled liquid pumped through element 110. A circulating system may, thus, be formed where fluid expelled at output 180 is re-cooled at the fluid source and re-directed into input 175. The temperature of the fluid source and/or element 110, which may include the rate at which cooling fluid is pumped through element 110, can be monitored and controlled by control unit 105. Thus, the temperature of cooling/heating element 110 can be controlled or programmed using control unit 105. As further shown in FIG. 1C, there can be a temperature difference, $\Delta T$, between regions of element 110. For example, heat from the target tissue may be transferred to the cooling fluid during treatment causing fluid near output 180 to have a higher temperature than the cooling fluid near input 175. Such $\Delta T$ may be reduced by reducing the size of element 110. In accordance with an embodiment of the invention, the configuration of the passages in element 110 and the corresponding application of element 110 to target tissue can account for any difference in temperature needed for treating various tissue targets. For example, the region of element 110 near exit 180 can be applied to treatment areas requiring a higher treatment temperature, and so forth. The passages of element 110 can, thus, be configured in accordance with the size, shape, formation, and so forth, of target tissue that require the various treatment temperatures. Cooling/heating fluid can also be pumped through element 110 in a pulsing manner.

Referring back to FIG. 1A, treatment interface 115 can be any type of interface between cooling/heating element 110 and the epidermis 160 for effecting treatment onto the epidermis 160, dermis 165 and fat cells 170. For example, treatment interface 115 may include a cooling (conductive) plate, a cooling fluid-filled vessel, a free-forming membrane 116 (for a complementary interface with an uneven epidermis), a convex cooling element (for example, as shown in FIG. 3), and the like. Preferably, treatment interface 115 comprises a heat conducting material that complements the epidermis 160 for maximum heat transfer between cooling/heating element 110 and the epidermis 160, dermis 165 and/or fat cells 170. For example, treatment interface 115 can be a fluid-filled vessel or a membrane so that the change in pressure from cooling element 110 caused by a pulsing flow of cooling fluid may be transferred to the target tissue. Furthermore, treatment interface 115 may simply be a chamber where cooling/heating fluid may be applied directly to the target tissue (epidermis 160, dermis and fat cells 170), for example by using a spraying device and the like.

Detector 120 can be a temperature monitor, for example, a thermocouple, a thermistor, and the like. Detector 120 may include any thermocouple type, including Types T, E, J, K, G, C, D, R, S, B, for monitoring tissue cooling. Detector 120 may also include a thermistor, which can comprise thermally-sensitive resistors whose resistances change with a change in temperature. The use of thermistors may be particularly advantageous because of their sensitivity. In accordance with an embodiment of the invention, a thermistor with a large negative temperature coefficient of resistance ("NTC") can be used. Preferably, a thermistor used for detector 120 may have a working temperature range inclusive of about −15° C. to 40° C. Furthermore, detector 120 can include a thermistor with active elements of polymers or ceramics. A ceramic thermistor may be most preferable as these can have the most reproducible temperature measurements. A thermistor used for detector 120 can be encapsulated in a protective material such as glass. Of course, various other temperature-monitoring devices can also be used as dictated by the size, geometry, and temperature resolution desired. Detector 120 can also comprise an electrode which can be used to measure the electrical resistance of the skin surface area. Ice formation within superficial skin structures like the epidermis or dermis causes an increased electrical resistance. This effect can be used to monitor ice formation within the dermis. Detector 120 can further consist of a combination of several measurement methods.

Detector 120 can, thus, extract, inter alia, temperature information from the epidermis 160, dermis 165 and/or fat cells 170 as feedback to control unit 105. The detected temperature information can be analyzed by control unit 105 based on inputted properties and/or parameters. For example, the temperature of fat cells 170 may be determined by calculation based on the temperature of the epidermis 160 detected by detector 120. Thus, treatment system 100 may non-invasively measure the temperature of fat cells 170. This information may then be used by control unit 105 for continuous feedback control of treatment unit 107, for example, by adjusting the energy/temperature of cooling/heating element 110 and treatment interface 115, thus maintaining optimal treatment temperature of target fat cells 170 while leaving surrounding epidermis 160 and dermis 165 intact. As described above, the cooling/heating element 110 can provide adjustable temperatures in the range of about $-10°$ C. up to $42°$ C. An automated temperature measurement and control sequence can be repeated to maintain such temperature ranges until a procedure is complete.

It is noted that adipose tissue reduction by cooling lipid-rich cells may be even more effective when tissue cooling is accompanied by physical manipulation, for example, massaging, of the target tissue. In accordance with an embodiment of the present invention, treatment unit 107 can include a tissue massaging device, such as a vibrating device and the like. Alternative a piezoelectric transducer can be used within treatment unit 107 in order to provide mechanical oscillation or movement of the cooling/heating element 110. Detector 120 can include feedback devices for detecting changes in skin viscosity to monitor the effectiveness of treatment and/or to prevent any damage to surrounding tissue. For example, a vibration detecting device can be used to detect any change in the resonant frequency of the target tissue (or surrounding tissue), which can indicate a change in tissue viscosity, being mechanically moved or vibrated by a vibrating device contained in treatment unit 107.

To further ensure that the epidermis 160 and/or the dermis 165 is not damaged by cooling treatment, an optical detector/feedback device can be used to monitor the change of optical properties of the epidermis (enhanced scattering if ice formations occur); an electrical feedback device can be used to monitor the change of electric impedance of the epidermis caused by ice formation in the epidermis; and/or an ultrasound feedback device may be used for monitoring ice formation (actually to avoid) in the skin. Any such device may include signaling control unit 105 to stop or adjust treatment to prevent skin damage.

In accordance with an embodiment of the invention, treatment system 100 may include a number of configurations and instruments. Algorithms that are designed for different types of procedures, configurations and/or instruments may be included for control unit 105.

Figure 1D:
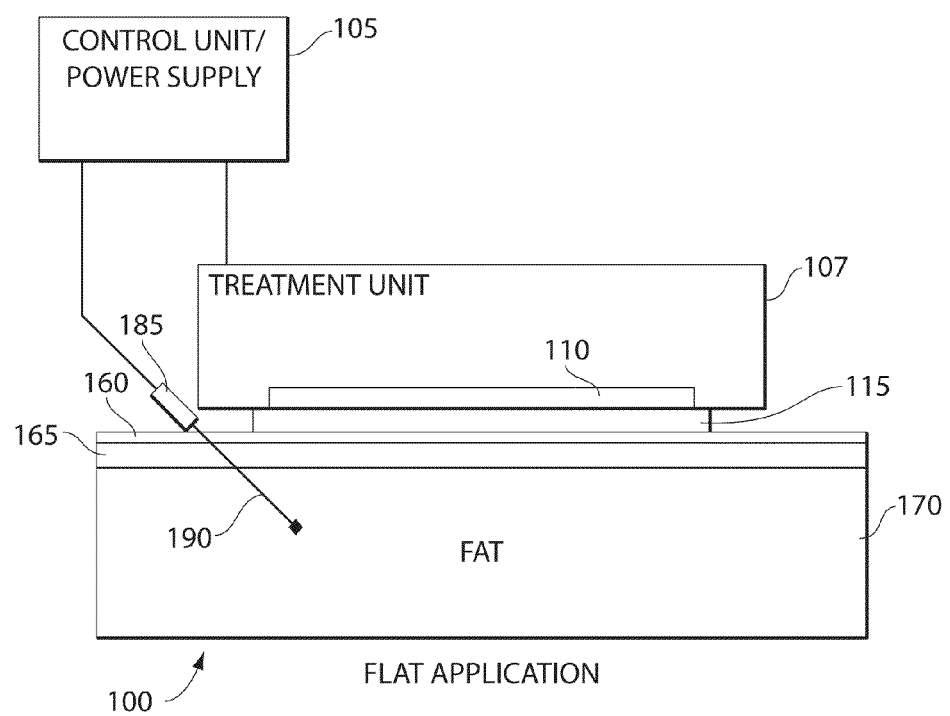
FIG. 1D illustrates a flat cooling treatment system with a probe controller.

As shown in FIG. 1D, treatment system 100 may include a probe controller 175 and a probe 180 for minimal invasive temperature measurement of fat cells 170. Advantageously, probe 180 may be capable of measuring a more accurate temperature of fat cells 170, thereby improving the control of treatment unit 107 and the effectiveness of treatment.

It is noted that treatment system 100 may be controlled remotely. For example, the link between control unit 105 and treatment unit 107 may be a remote link (wired or wireless) providing control unit 105 remote control over cooling/heating element 110, treatment interface 115, probe controller 175, and probe 180.

While the above exemplary treatment system 100 is illustrative of the basic components of a system suitable for use with the present invention, the architecture shown should not be considered limiting since many variations of the hardware configuration are possible without departing from the present invention.

Figure 2A:
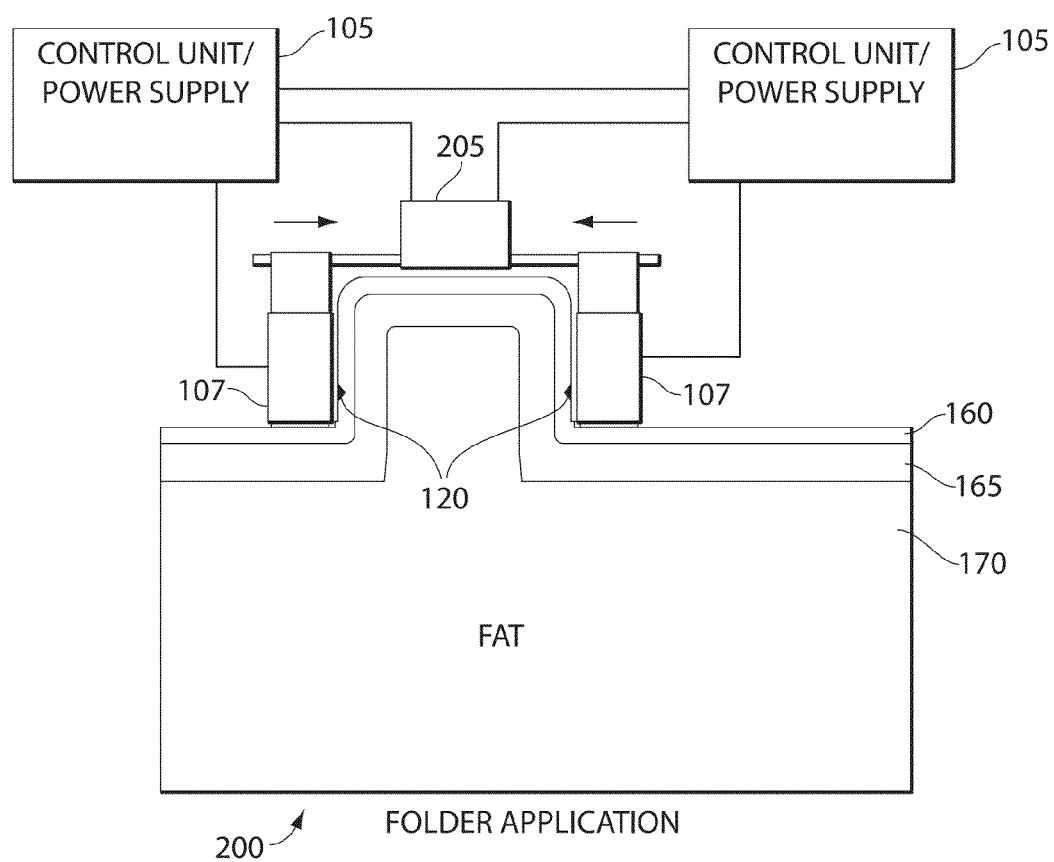
FIG. 2A illustrates a treatment system for cooling lipid-rich cells within a skin fold.

FIG. 2A illustrates a treatment system 200 for cooling fat cells 170 by folding the target tissue in accordance with an embodiment of the invention. As shown in FIG. 2A, treatment system 200 may include corresponding control units 105 and treatment units 107 on two sides coupled to a compression unit 205. Compression unit 205 may be adapted to pull treatment units 107 together, thereby folding (or "pinching") target tissue (epidermis 160, dermis 165 and fat cells 170) up between treatment units 107. The treatment interface 115 of the respective treatment units 107 on either side of the target tissue may thus cool fat cells 170 from multiple sides with greater effectiveness, as described above. Detectors 120 can be included to measure and monitor the temperature of the target tissue. As shown in FIG. 2A, control units 105 may be connected to form an integrated system. In accordance with an embodiment of the present invention, the various components of system 200 may be controlled using any number of control unit(s).

As described before, physical manipulation of target tissue may improve the effectiveness of cooling treatment. In accordance with an embodiment of the present invention, compression unit 205 may vary the force with which treatment units 107 are pulled together around the target tissue (epidermis 160, dermis 165 and fat cells 170). For example, compression unit 205 can apply a pulsing force for alternately tightening and loosening the fold (or "pinch") of the target tissue. Resistance to the tightening can further be monitored for detecting any changes in the characteristics (for example, the viscosity) of the target tissue, and thus ensuring the effectiveness and safety of the treatment.

Figure 2B:
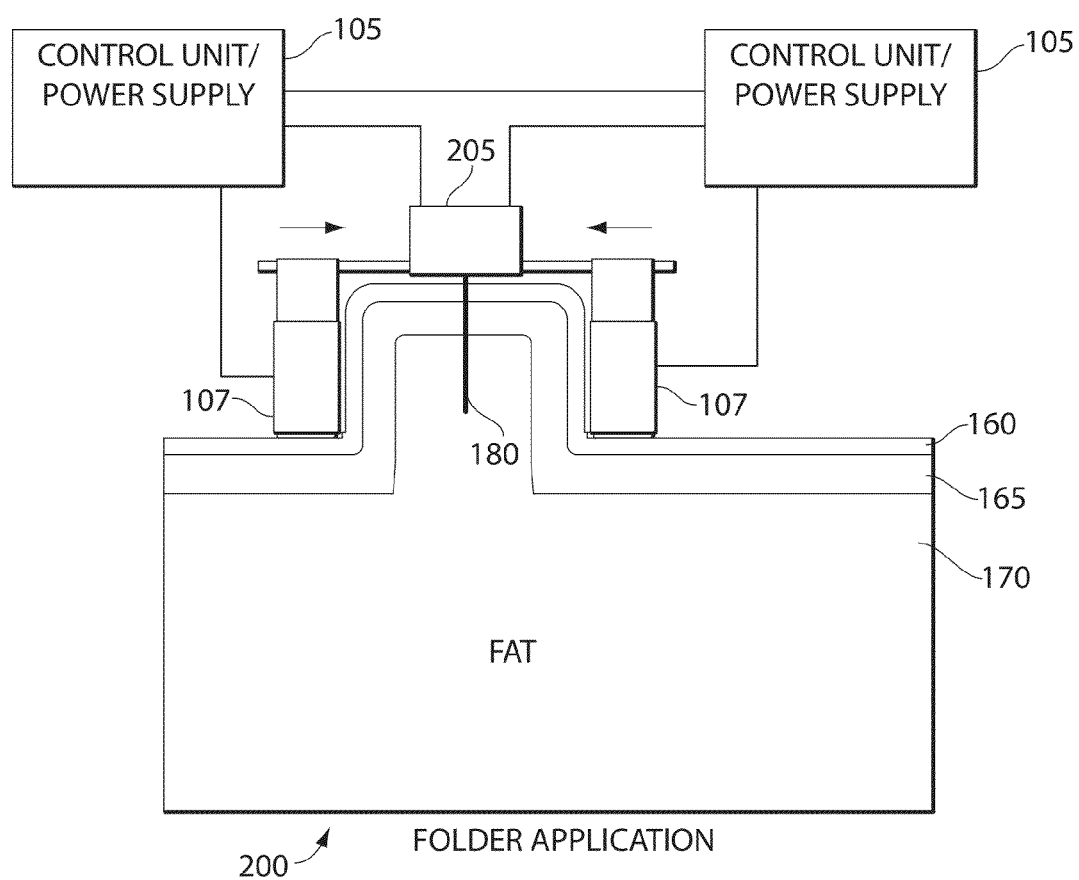
FIG. 2B illustrates a treatment system for cooling lipid-rich cells within a skin fold with a probe controller.

FIG. 2B illustrates system 200 with a probe 180 similar to that of system 100 shown in FIG. 1C for minimal invasive temperature measurement of fat cells 170. As described above, probe 180 may be capable of measuring a more accurate temperature of fat cells 170, thereby improving the control of treatment unit 107 and the effectiveness of treatment.

Figure 3A:
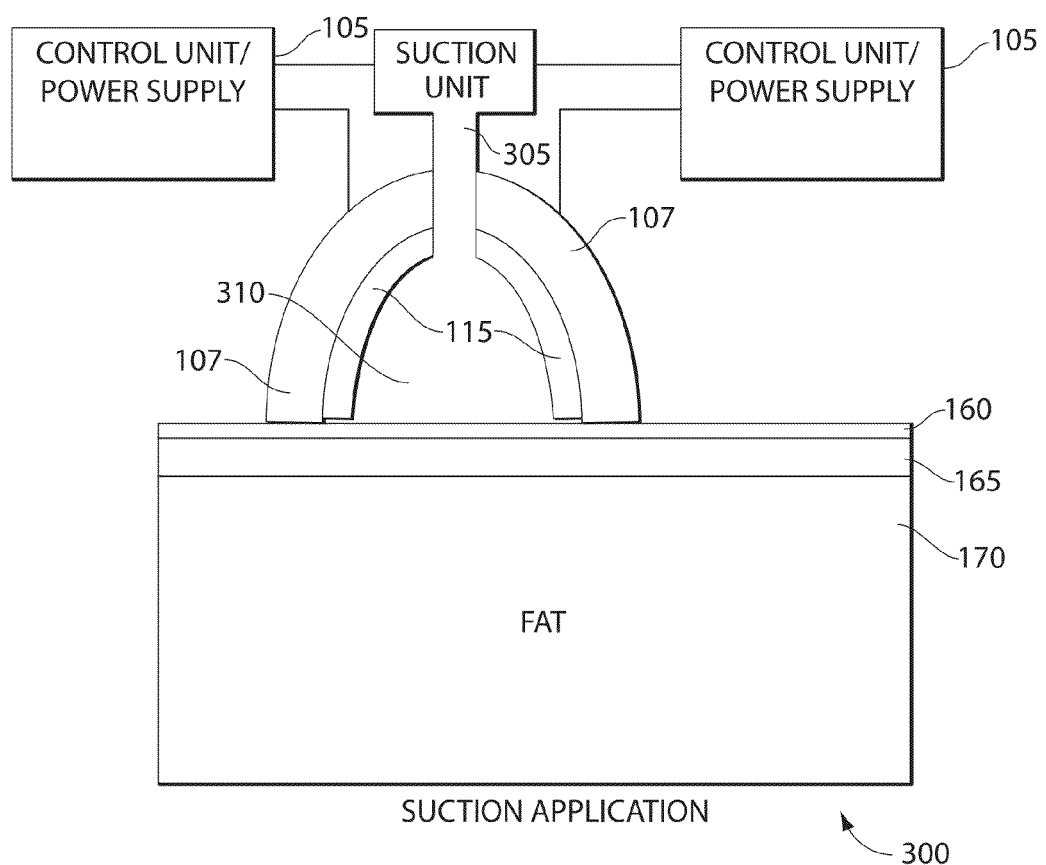
FIG. 3A, B illustrates a treatment system that includes a suction unit.
Figure 3B:
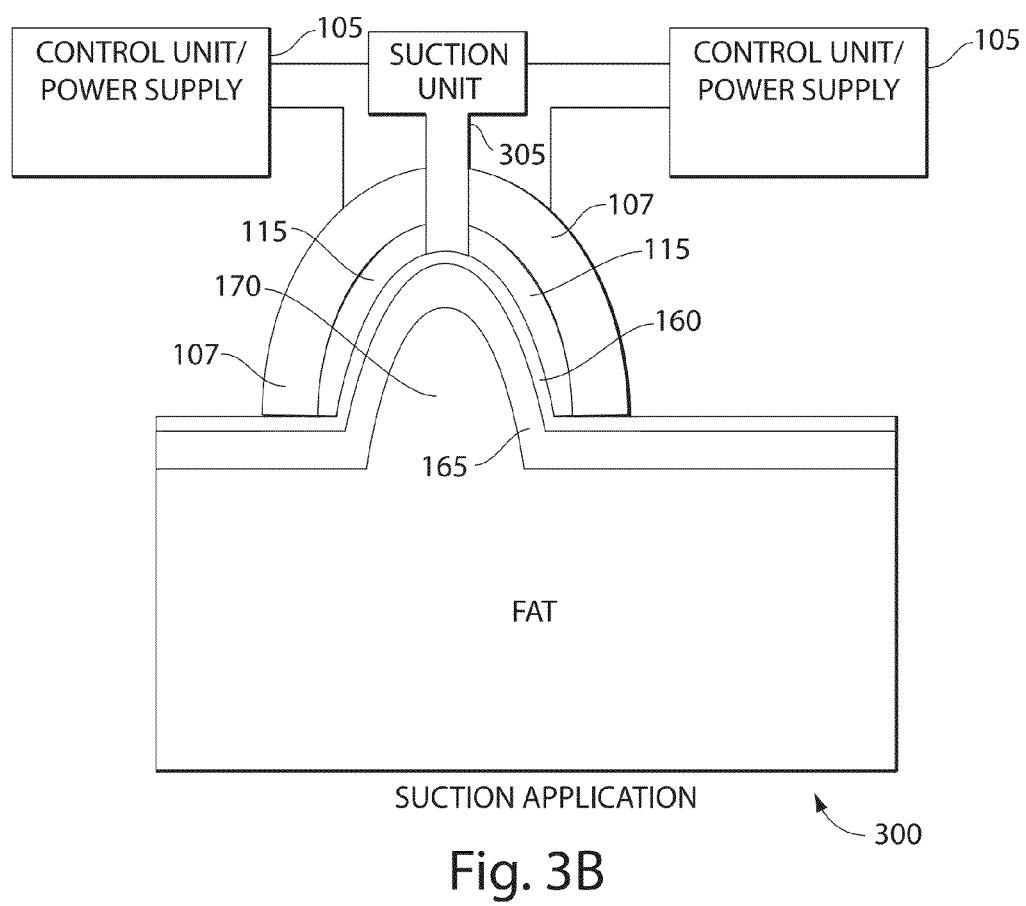

FIGS. 3A and 3B are diagrams showing a treatment system 300 in accordance with an embodiment of the present invention. As shown in FIG. 3A, system 300 may include a suction unit 305, and treatment unit 107 may include treatment interface 115 having a curved surface, which for example forms a dome, for forming and containing a chamber 310 above the epidermis 160. As shown in FIG. 3B, suction unit 305 may be activated to draw the air from chamber 310 such that target tissue (epidermis 160, dermis 165 and fat cells 170) is pulled up into contact with treatment interface 115. Advantageously, treatment interface 115 may surround target fat cells 170 for more effective cooling. Treatment interface 115 can consist of a solid stiff or flexible material, which is in contact with the skin or a thermal coupling agent between the skin surface and the treatment unit. The surface of the interface 115 can also have multiple openings connected to suction unit 305. The skin is partially entered into these multiple openings, which can increase the total surface area of the epidermis 160 in thermal contact to the treatment interface (e.g., stretching of the skin). Stretching of the skin decreases the thickness of the epidermis and dermis, facilitating cooling of the fat 170. A number of detector(s) 120 and/or probe(s) 180 can be included in treatment system 300 for monitoring tissue temperature during treatment, as described above with reference to FIGS. 1A, 1C, 2A and 2B, detailed description of which will not be repeated here.

Figure 4:
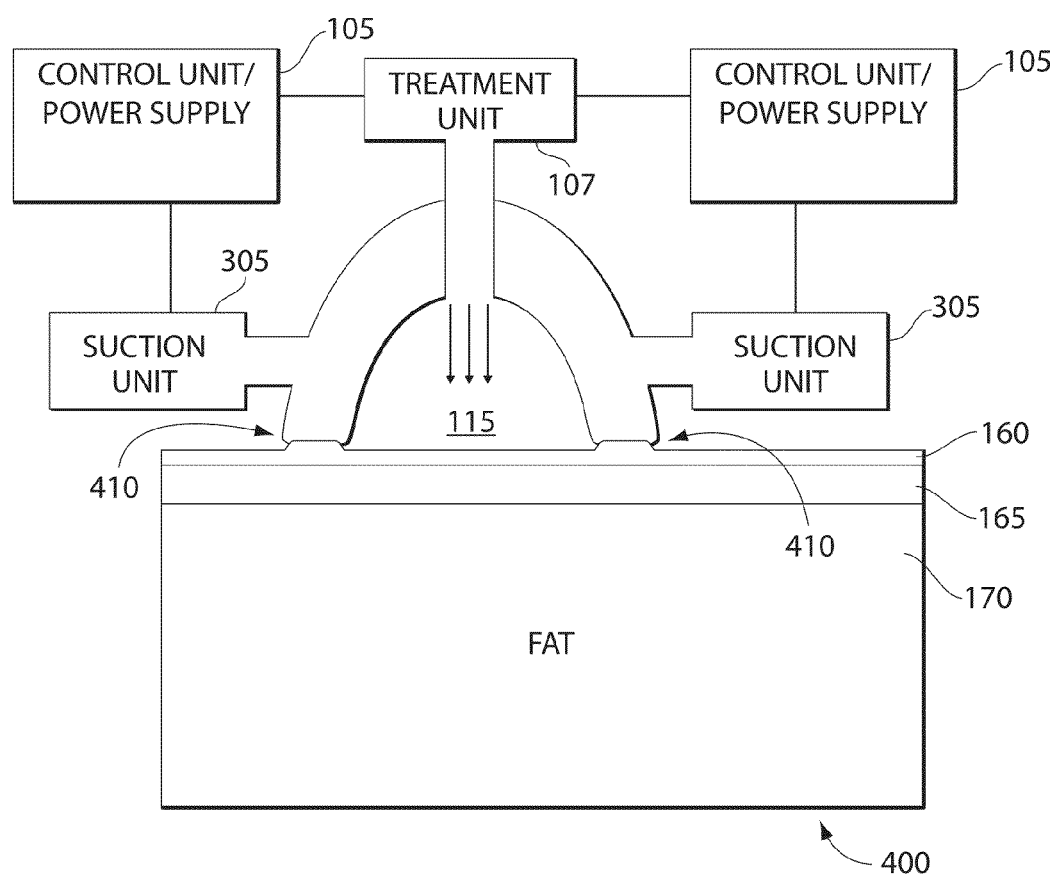
FIG. 4 illustrates a treatment system that is combined with suction system to provide treatment of an isolated area.

FIG. 4 illustrates a treatment system 400 in accordance with an embodiment of the invention. As shown in FIG. 4, suction unit 305 can be connected to a ring opening around treatment interface 115 so that, when activated, a suction seal 410 is formed with the epidermis 160 around treatment interface 115. As a result, treatment can be effected at treatment interface 115 to an isolated target tissue area. Advantageously, the subject or body part may be immersed in a warming bath and the treatment at interface 115 can be unaffected. Consequently, treatment area can be increased while a surrounding warming environment can prevent general hypothermia.

Figure 5A:
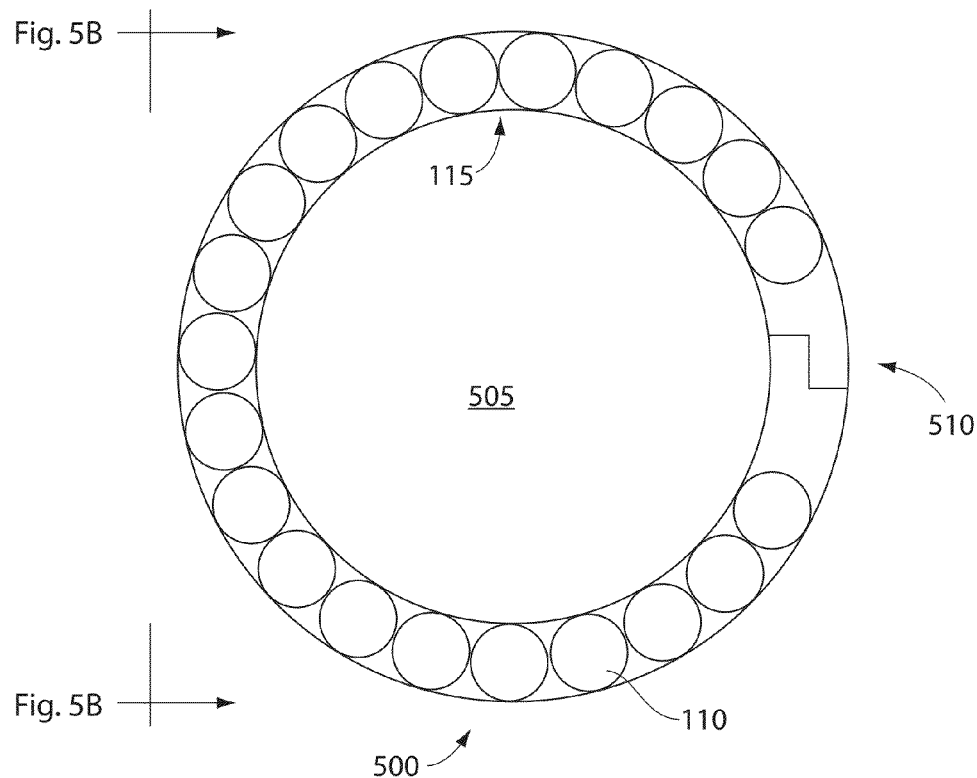
FIG. 5A, B illustrate a treatment system which can enclose circumferentially a target tissue mass.
Figure 5B:
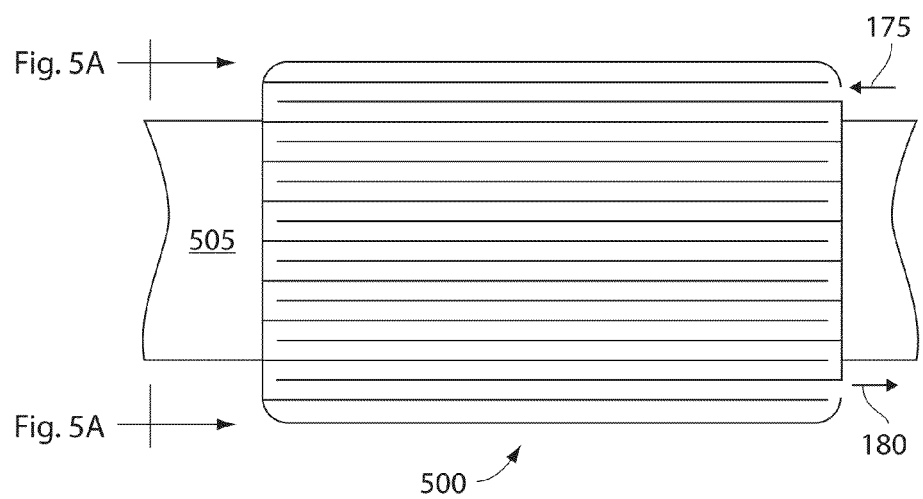

FIGS. 5A and 5B are diagrams showing a treatment system 500 in accordance with an embodiment of the present invention. As shown in FIGS. 5A and 5B, treatment system 500 may form a band (or cylinder) around a target tissue mass 515. Treatment system 500 may comprise any flexible or rigid material. Cooling/heating fluid can be pumped through treatment system 500 via input 175 and output 180, as shown in FIG. 5B. Cooling/heating element 110 can be formed by an internal vessel or a network of passages, such as tubing and the like. Heat transfer with target tissue mass 515 can be effected via treatment interface 115, which can include any heat conducting material. Treatment system 500 can further include a fastening mechanism 510, such as a hook and loop fastener and the like, for fastening and wrapping around tissue mass 515. Furthermore, treatment interface 115 can include a flexible material such that the pressure of cooling fluid pumped through treatment system 500 can be transferred to the target tissue 515. For example, with reference to FIG. 5A, treatment system 500 can apply inward pressure to target tissue mass 515. Target tissue mass 515 can be any section, body part or extremity of a subject. For example, target tissue mass 515 can be an arm, the upper or lower leg, the waist, and so forth, of a subject. The pressure and flow of the cooling fluid in system 500 can be controlled by control unit 105 to an optimal treatment temperature and/or pressure. A tight fit around tissue mass 515 and increased inward pressure can also allow for the subject to be immersed in a warming bath. As described before, fluid flow can be a pulsing flow.

The present invention is additionally described by way of the following illustrative, non-limiting Examples, that provide a better understanding of the present invention and of its many advantages.

EXAMPLES

Example 1

Selective Damage to Fatty Tissue by Controlled Cooling In Vivo

Methods of the present invention were carried out on a white, 6 months old, female, Hanford miniature pig ("Pig I") and a black, 6 months old, female Yucatan Miniature Pig ("Pig II"). The pigs were anesthetized using Telazol/Xylazine (4.4 mg/kg im+2.2 mg/kg im). Inhalant anesthetics (Halothane or Isoflurane (1.5-3.0%) with Oxygen (3.0 L/min) was delivered by mask and filtered with an F-Air canister only if the injectable anesthetics did not provide enough somatic analgesia. Several test sites were be marked with micro tattoos by applying India Ink to the corners of each test sites. After mapping of the test sites cold exposures were performed using a cooling device as described in FIG. 1A. The area of the treatment interface was a flat area of the size of 2×4 cm$^2$ with a built-in temperature sensor. The interface was in thermal contact with a thermoelectric chiller, which was electronically regulated by a control unit such that the temperature at the surface of the interface was kept constant to a pre-set temperature. During the cold exposure the cooling device was applied to the skin with minor to moderate pressure that did not cause significant mechanical compression of blood flow. The cooling element was applied to the skin without any manipulation of the surface profile.

Various combinations of pre-set cooling interface temperatures and exposure times were tested. For some sites a thermo-conductive lotion was applied between the skin and the cooling interface. This thermoconductive lotion consisted mainly of glycerol. Pig I was observed for 61 days until excision biopsies from all test sites were procured and the pig was sacrificed. From test Site C there was an additional punch biopsy procured at day 2.

The biopsies were processed for routine light microscopy and stained with Hematoxylin & Eosin. The indicated temperature is that of the applied cooling element. Table 1 depicts the parameters of the cooling application and the results obtained at various sites in Pig I:

TABLE 1

| Site | Temperature | Time | Lotion | Results |
| --- | --- | --- | --- | --- |
| A | −6° C. | 1 minute | + | At 61 days:<br>No epidermal damage.<br>No dermal damage.<br>No obvious indentation.<br>No obvious histological alterations. |
| B | −6° C. | 1 minute | − | At 61 days:<br>No epidermal damage.<br>No dermal damage.<br>No obvious indentation.<br>No obvious histological alterations. |
| C | −6° C. | 5 minutes | + | At 61 days:<br>No epidermal damage.<br>No dermal damage.<br>Indentation due to loss of subcutaneous adipose tissue (1 week to 61 days).<br>Decreased average size of adipocytes at a depth of between about 3-6 mm.<br>Obvious histological damage to the adipose tissue.<br>At 2 days:<br>Tissue inflammation and panniculitis. |

TABLE 1-continued

| Site | Temperature | Time | Lotion | Results |
|------|-------------|------|--------|---------|
| D | −3.5° C. | 5 minutes | + | At 61 days:<br>No epidermal damage.<br>No dermal damage.<br>No obvious indentation.<br>Borderline histological damage to the adipose tissue.<br>Decreased average size of adipocytes. |
| E | Control | | | Normal-no changes within the epidermis, dermis and subcutaneous adipose tissue. |

Pig II was observed for 50 days until excision biopsies from all test sites were procured and the pig was sacrificed. From test Site E an additional biopsy was procured at day 17. The biopsies were processed for routine light microscopy and stained with Hematoxylin & Eosin as described above. The indicated temperature is that of the applied cooling element. Table 2 depicts the parameters of the cooling application and the results obtained at various sites in Pig II:

TABLE 2

| Site | Temperature | Time | Lotion | Results |
|------|-------------|------|--------|---------|
| C | −6° C. | 5 minutes | − | At 50 days:<br>Pronounced indentation (2-3 mm) due to loss of subcutaneous adipose tissue.<br>No epidermal damage.<br>No dermal damage.<br>No pigmentary changes, however, decreased size of adipocytes and histological damage to adipose tissue. |
| D | −8° C. | 5 minutes | − | At 50 days:<br>Pronounced indentation (2-3 mm) due to loss of subcutaneous adipose tissue.<br>No epidermal damage.<br>No dermal damage.<br>No pigmentary changes, however, there was damage to the adipocytes to a depth of about 6 mm.<br>Decreased size of adipocytes and histological damage to adipose tissue. |
| E | −9° C. | 5 minutes | − | At 50 days:<br>Pronounced indentation (2-3 mm) due to loss of subcutaneous adipose tissue.<br>No epidermal damage.<br>No dermal damage.<br>No pigmentary changes, however, there was damage to the adipose cells to a depth of about 6 mm.<br>Decreased size of adipocytes and histological damage to adipose tissue.<br>At 17 days:<br>Signs of panniculitis. |
| F | −22° C. | 5 minutes | − | At 50 days:<br>Pronounced epidermal damage with pronounced hypopigmentation.<br>Scar formation with dermal contraction and complete ablation of the subcutaneous adipose tissue. |

Figure 6:
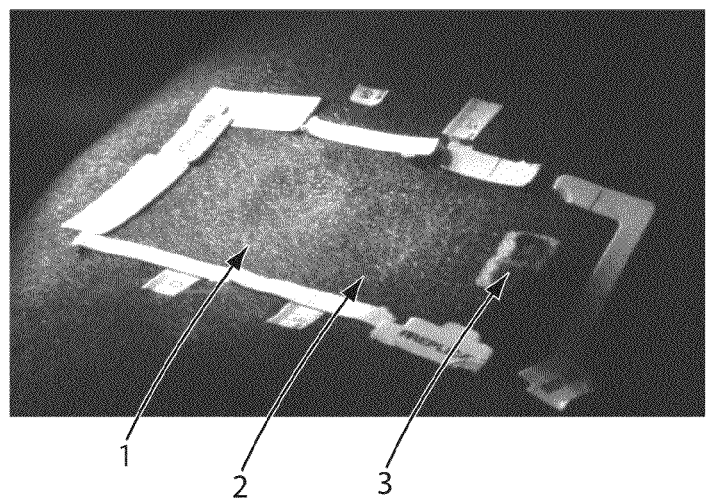
FIG. 6 depicts an image of the skin surface showing indentation after 17 days at some areas matching cold exposure sites.

FIG. 6 depicts an image of the skin surface of test Sites D, E and F of Pig II, 17 days after exposure. An indentation that matches the site of the cold exposure can be seen at 1, which matches test Site D and 2, which matches test Site E. No abnormal epidermal changes can be seen at these test sites. At 3, which matches the test Site F, where aggressive cooling methods were applied, damage to the epidermis is pronounced (e.g., loss of pigmentation and a central crust formation).

Figure 7A:
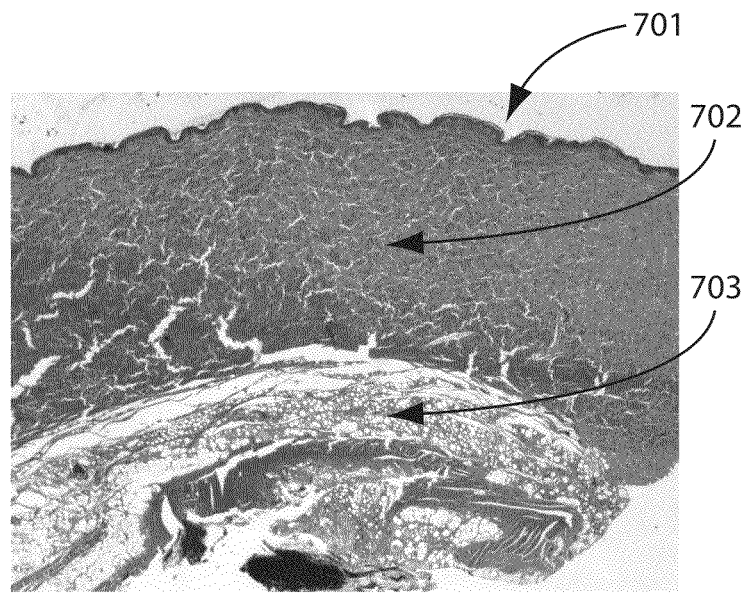
FIG. 7A shows the low magnification view and FIG. 7B shows the high magnification view.
Figure 7B:
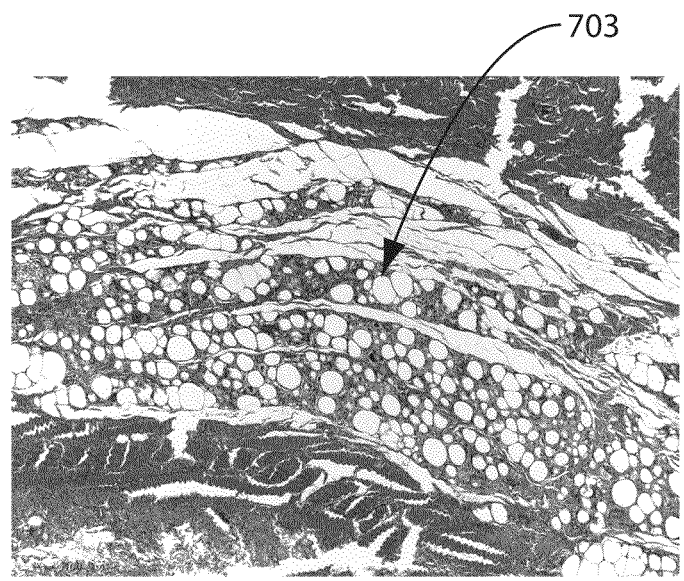

FIG. 7 depicts histology of test Site E (Pig II), 17 days after cold exposure at −9° C. for 5 minutes, in samples taken from an area below the site of cold exposure. FIG. 7A depicts a low power magnification (1,25×) and FIG. 7B depicts a close up with medium power magnification (5×) of the same specimen. The epidermis 701, dermis 702, subcutaneous adipose 703 and muscle layer 704 are shown. The histology reveals signs of lobular and septal panniculits within subcutaneous adipose 703, which is an inflammation of the adipose tissue. The average size of fat cells is decreased compared to the sample from the unexposed area. No evidence of tissue alterations is seen in the epidermis, dermis or muscle layer.

Figure 8A:
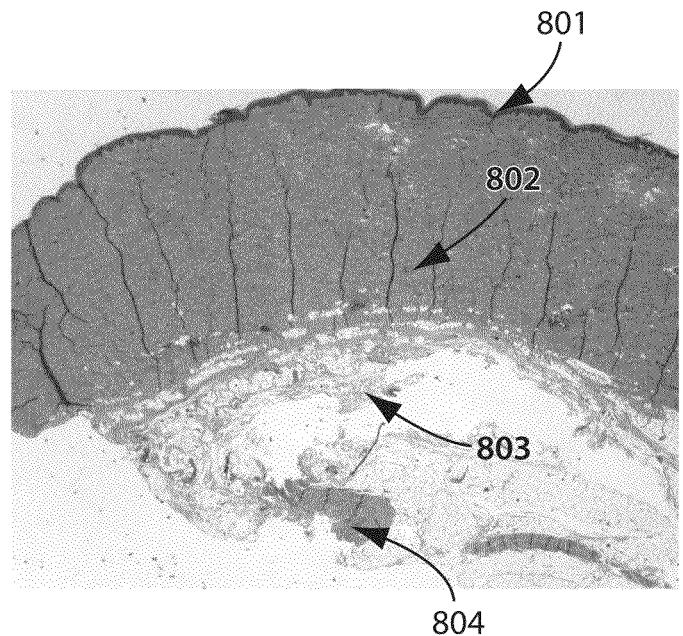
FIG. 8A, B depicts Site C; 8 C, D depicts Site E; and 8 E, F depicts Site F; each of which show histology of the subcutaneous adipose tissue 17 days after cold exposure (Pig II, Site C, E and F).
Figure 8B:
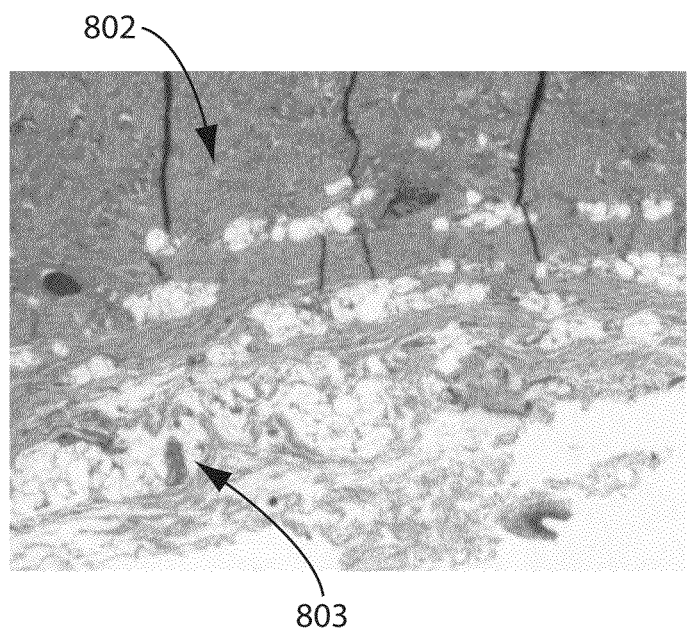
Figure 8C:
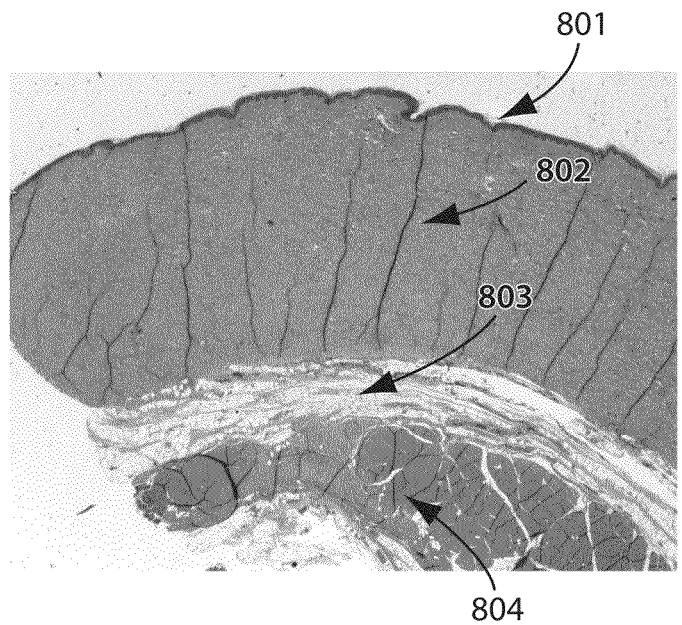
Figure 8D:
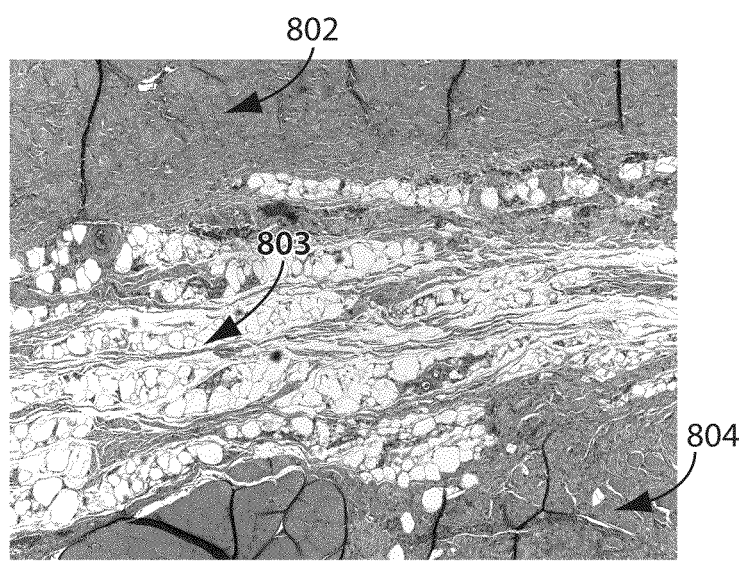
Figure 8E:
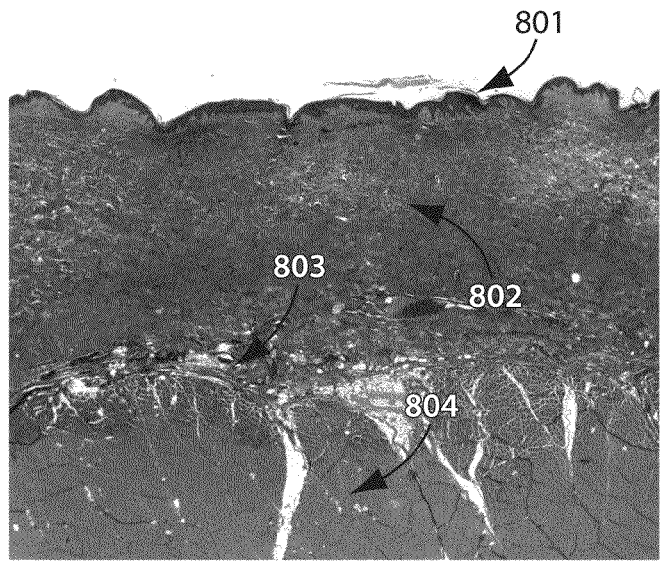
Figure 8F:
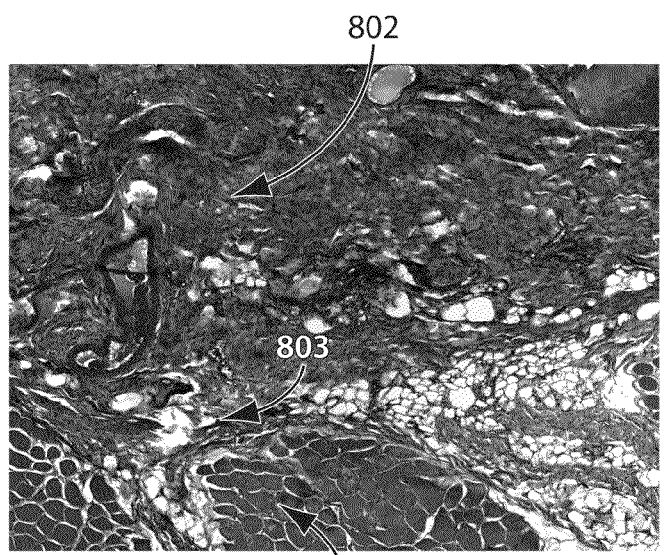

A decrease in subcutaneous adipose tissue was demonstrated by clinical observation of indentation within the skin surface at the precise site of cooling, as well as by histology (Hematoxylin & Eosin staining). FIG. 8A, B, C, D, E, and F depicts histology 50 days after exposure with low power magnification of 2.5× (FIGS. 8A, 8C and 8E) and medium power magnification of 5× (FIGS. 8B, 8D and 8F) of test Site C (FIGS. 8A and 8B), test Site E (FIGS. 8C and 8D) and test Site F (FIGS. 8E and 8F). The epidermis 801 and dermis 802 is not damaged in test Sites C and E while the more aggressive cooling regime applied to test Site F resulted in damage to the epidermis and dermis (e.g., scar formation and inflammation can be seen). The subcutaneous adipose 803 shows a decrease of adipocyte size and structural changes (e.g., apparent condensation of the fat cell layer with fibrous septae is included in the condensated fat layer). As a result of the aggressive cooling regime applied to test Site F, almost the entire layer was removed, leaving only some residual fat cell clusters. Thus, where an aggressive cooling regime is applied (test Site F) non-selective and pronounced damage is observed in the epidermis and dermis.

Taken together, the results demonstrate that selective disruption of subcutaneous adipose tissue is achieved using cooling methods of the present invention without causing damage to the epidermis and dermis.

Measurement of temperature during skin surface cooling at −7° C. applied with pressure sufficient to stop skin blood flow, was performed to illustrate the time-and depth-dependence of cooling, in a live pig. Thermocouples inserted at depths of 0, 2, 4, and 8 millimeters were used to record temperature. Although the conditions of this experiment were not ideal (the skin cooler did not maintain strictly −7° C. at the surface), it is clear that cooling of the dermis (2 mm) and fat (4 mm, 8 mm) occurred generally as expected (see for example, FIG. 10).

sure was performed with a convex round copper plate attached to a heat exchanger, which was chilled by a circulating cooling agent tempered to −7° C. The exposure time ranged between 600 to 1200 s. Table 3 depicts the parameters of the cooling application and the results obtained at various sites in Pig III. The cold plate had three central openings of approximately 1 mm in diameter through which thermocouples were placed to monitor the temperature profile at different depth of the tissue during cold exposure. The cold exposure device, shown in FIG. 9, was firmly held to the test site during cold exposure. Cold exposures were performed on two different experimental days, one week apart. On the first experimental day the thermocouples were occasionally displaced during the cold exposure leading to a 0.5 mm variability of the thermocouple depth measurement. An additional set of exposures with thermocouples were performed on the second experimental day at well-defined depths with minimal to no variability in the depth of the thermocouples. The location of the thermocouples on the first experimental day for test Sites 1,2,3,7,11 and 12 was at 2.5, 4.5 and 10 mm depth (+/−0.5 mm). Test Sites 14,15,16 and 18 were treated on the second experimental day at a thermocouple depth of 2, 4 and 8 mm, with minimal to no displacement. A certain variability of the thermocouple depth may still be present due to tissue compression during the cold exposure. A glycol containing solution was used to ensure good thermal contact at the skin surface. The pig was observed for 3½ months after treatment, until sacrificed and the tissue of the test sites harvested for analysis. Table 3 depicts the parameters of the cooling application and the results obtained at various sites in Pig III:

TABLE 3

| Site | Temperature (coolant agent) | Exposure time | Location | $Temp_{min}$ @ depth | $Temp_{min}$ @ depth | $Temp_{min}$ @ depth | Indentation $3^{1/2}$ months | Relative decrease of superficial fat layer @ 3½ months |
|---|---|---|---|---|---|---|---|---|
| 1 | −7° C. | 5 minutes | Flank | 0° C. @ 2.5 mm | 7° C. @5 mm | 24° C. @ 10 mm | + | 66% |
| 2 | −7° C. | 5 minutes | Flank | −2° C. @ 2.5 mm | N/A | 21° C. @ 10 mm | + | |
| 3 | control | | Flank | | | | − | 9% |
| 7 | −7° C. | 10 minutes | Abdomen | −3° C. @ 2.5 mm | 7° C. @ 5 mm | 19° C. @ 10 mm | + | |
| 9 | control | | Abdomen | | | | | |
| 11 | −7° C. | 10 minutes | Buttock | N/A | N/A | 12° C. @ 10 mm | ++ | 79% |
| 12 | −7° C. | 10 minutes | Buttock | −4° C. @ 2.5 mm | N/A | 13° C. @ 10 mm | + | 57% |
| 13 | −7° C. | 10 minutes | Buttock | −4° C. @ 2 mm | N/A | 7° C. @ 10 mm | + | |
| 14 | −7° C. | 21 minutes | Buttock | −4° C. @ 2 mm | 3° C. @ 4 mm | 12° C. @ 8 mm | + | |
| 15 | −7° C. | 11 minutes | Buttock | −4° C. @ 2 mm | 1° C. @ 4 mm | 12° C. @ 8 mm | + | |
| 16 | −7° C. | 10 minutes | Buttock | −4° C. @ 2 mm | 0° C. @ 4 mm | 14° C. @ 8 mm | ++ | |
| 18 | −7° C. | 15 minutes | Flank | −3° C. @ 2 mm | N/A | 15° C. @ 8 mm | + | 66% |

Example 2

Temperature Profile Measurements at Various Tissue Depths

This study was performed using a 6-months old female black, hairless Yucatan Minipig (Sinclair Research Center, Columbia, Mo.). The pig will was anesthetized using Telazol/Xylazine (4.4 mg/kg im+2.2 mg/kg im). Inhalant anesthetic (Halothane or Isoflurane (1.5-3.0%) with Oxygen (3.0 L/min) was delivered by mask and filtered with an F-Air canister only if the injectable anesthetic did not provide enough somatic analgesia. The test sites were marked with micro tattoos by applying India Ink to the corners of each test site and inserting hypodermic needles into such test site corners. The cold expo- The test sites were exposed to the device, set to a coolant temperature of −7° C. and exposed for 600 to 1200 s. The dermis hardened immediately after the cold exposure, as determined by palpation, and became viscose as it returned to its normal temperature, approximately a minute after exposure. There was no epidermal damage or alteration evident by close-up examination with polarized magnifier lens minutes after exposure. There was no blister formation and Nikolsky-sign was negative. During the entire survival period there was no gross damage to the epidermis. No crusting, blister or pronounced pigmentary changes were observed. Some test sites exhibits a minor increase in epidermal pigmentation. This mild hyperpigmentation could be removed after few months by gentle rubbing of the epidermis.

The temperature measurements of the thermocouples depended on depth, body location, and the pressure with which cooling was applied. The temperature plots at different tissue depths during the cold exposure are shown in FIGS. 10 A-J for various test sites and are also summarized in Table 3.

For some test sites, temperature oscillations that might be related to a nearby blood vessel was observed. Some temperature plots were not considered due to movements or misplacement of the thermocouple (labeled 'error' in table 3). The temperature within the deep dermis or superficial fat layer is within the range of −2° C. to −4° C. The temperature within 4-5 mm depth is within the range of about 0° C. to 7° C. depending on variations in contact pressure and anatomical area. This location demonstrated a high variability of the different temperature plots. The temperature within 8-10 mm depth, which corresponds to a depth within the subcutaneous fat layer had a temperature in the range of 7-24° C.

Histology of a control (Site 9) and cold exposed site (Site 8) (−7° C., 600 s) was procured 6 days post exposure and analyzed by a dermatopathologist. The following was described at the control and the cold exposed site:

The epidermis of both samples is normal and exhibits basket-woven stratum corneum with normal thickness, normal rete ridges as compared to the control. Within the cold exposed site there is a mild perivascular, lymphocytic infiltrate present. However no frank signs of vasculitis present in both samples.

Figure 11:
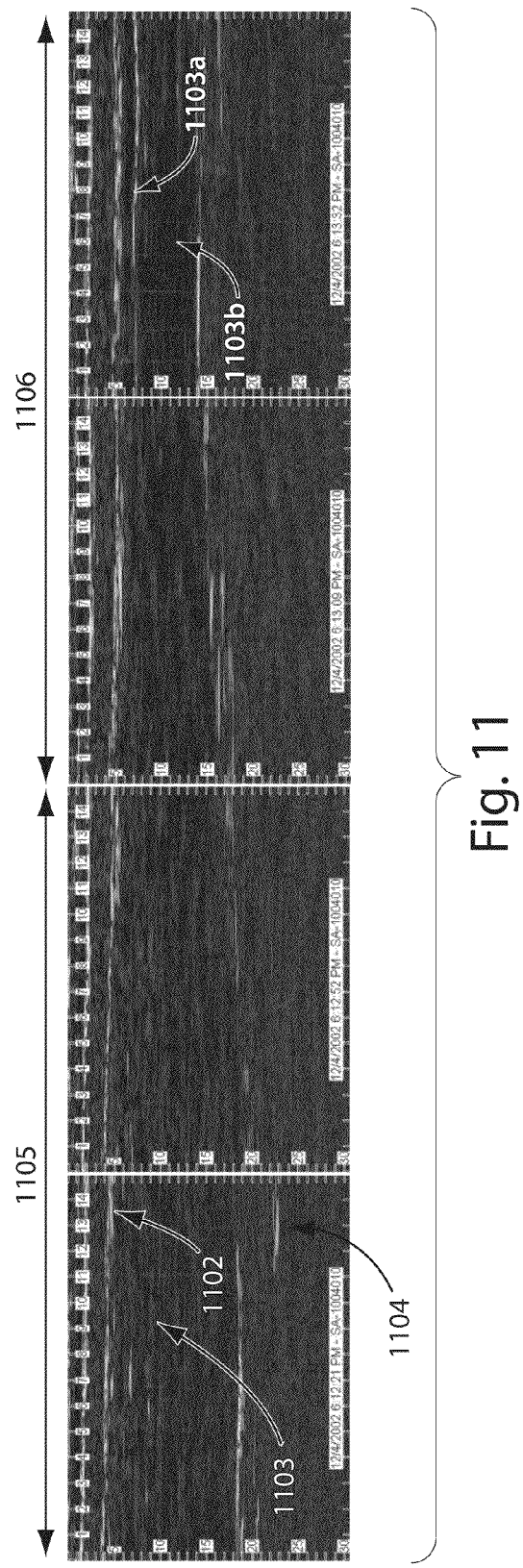
FIG. 11 depicts an ultrasound image of test Site 11, 3.5 months after exposure.

The subcutaneous fat of the control exhibit the normal morphology. The subcutaneous fat of the cold exposed site exhibits clear signs of lobular and septal panniculitis. Most of the adipocytes are surrounded by lymphocytic infiltrate with occasional lipid containing macrophages. The thickness of the subcutaneous septae is increased. Mild vascular changes however no frank signs of vasculitis. Three and one half months after the cold exposure the pig was sacrificed and tissue at the exposure sites was harvested by full thickness excision, after 20 MHz ultrasound imaging was performed through selected test sites. The in-vivo ultrasound images clearly demonstrated loss of fatty tissue in the area of treatment by skin cooling vs. the non-cold exposed surrounding tissue. An in-vivo ultrasound image 3½ months after cold exposure is shown in FIG. 11.

The harvested tissue was cut macroscopically through the test sites and images were taken from the macroscopic tissue cross-sections. The macroscopic cross sections of Sites 1,3, 11,12 and 18 are shown in FIG. 13 A-E. A decrease of the thickness of the subcutaneous fat layer was observed for all cold exposed sites vs. the non-cold exposed adjacent fat layer. The macroscopic cross sections matched well with the ultrasound images. Two different compartments within the subcutaneous fat could be identified, a superficial fat layer and a deep fat layer. Thickness of the superficial fat layer was dramatically reduced at sites of cold treatment, while the deep fat layer was not significantly changed. The percentage of decrease of the superficial fat layer inside the test area vs. outside is listed for some test sites in Table 3. A change of the subcutaneous fat layer was observed for cold exposed Sites 1,11,12 and 18. The average decrease of thickness for the superficial fat layer within the evaluated test sites was 47%. For the unexposed control side, no significant decrease of thickness was found in either fat layer.

These examples confirm that it is possible in a pig model to achieve selective tissue damage of the subcutaneous adipose tissue by external cooling within a specific range of external cooling temperature and exposure time, without significant damage to the epidermis and dermis. Removal of subcutaneous fat was also demonstrated by an obvious indentation at the treated skin surface, which matched exactly with the cooling exposure, and with the measurements of the fat layer in relation to the cold exposure site by ultrasound and macroscopic cross sections after sacrifice. Pronounced histological changes, which were selective to the subcutaneous adipose tissue were observed 6 days after cold exposure. Histologically a panniculitis with a decrease in fat cell size was observed. There was evidence that the response to the cold can vary for different sites and that the more superficial fat layer is more affected by tissue loss than the deeper fat layer. The results of Pig III however imply that there is enhanced fat removal at the superficial fat layer vs. the deeper layer. The explanation for this is a) the superficial fat layer is exposed to colder temperatures because of the gradient and/or b) the deeper fat layer in pigs may be less susceptible to selective cold damage.

Figure 9:
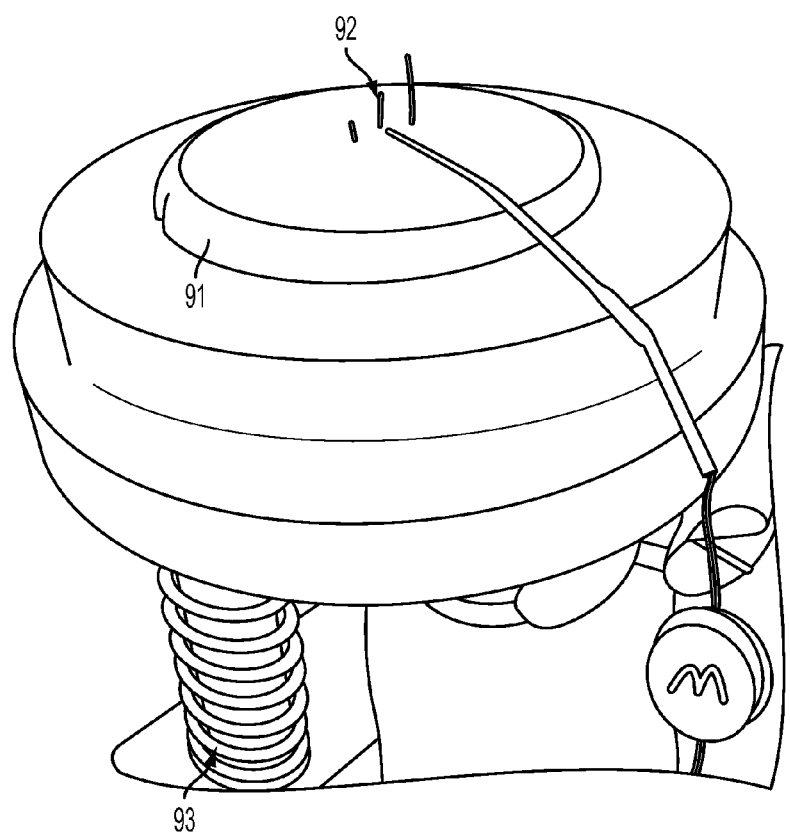
FIG. 9 depicts an image of the device used to administer cooling to Pig III.
Figure 10A:
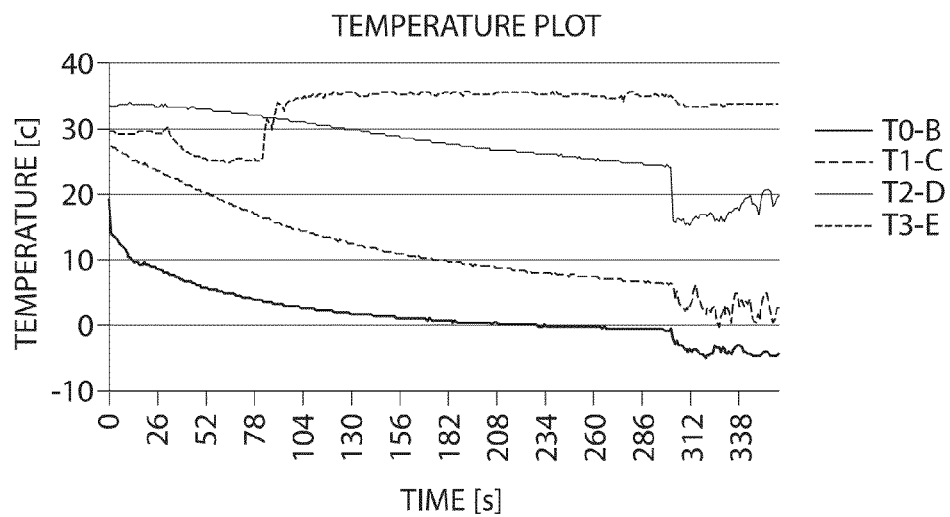
FIG. 10A, B, C, D, E, F, G, H, I, and J depicts temperature plots of the exposure sites 1, 2, 7, 11, 12, 13, 14, 15, 16 and 18 of Pig III in various tissue depths.
Figure 10B:
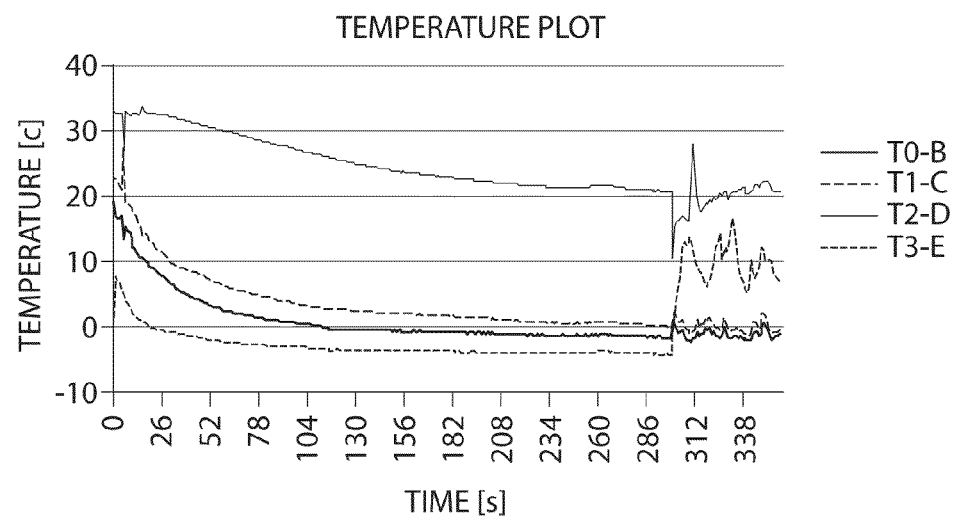
Figure 10C:
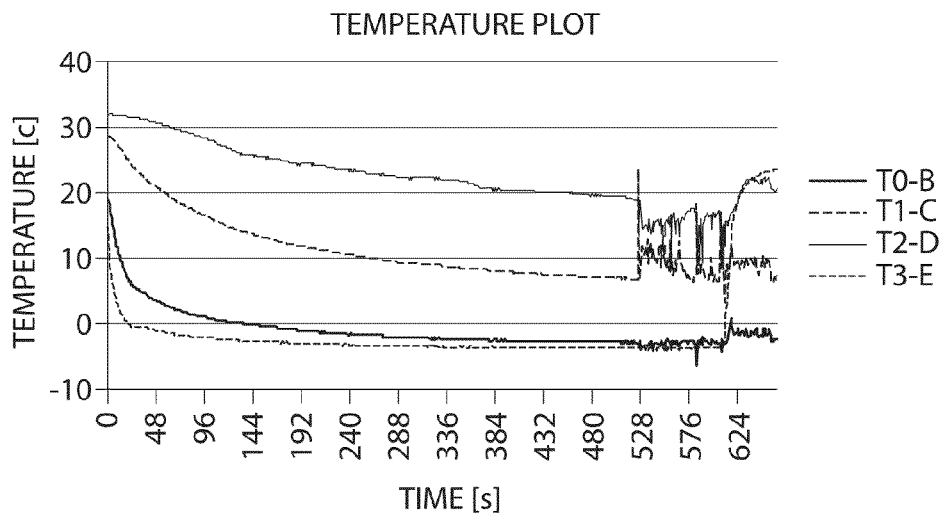
Figure 10D:
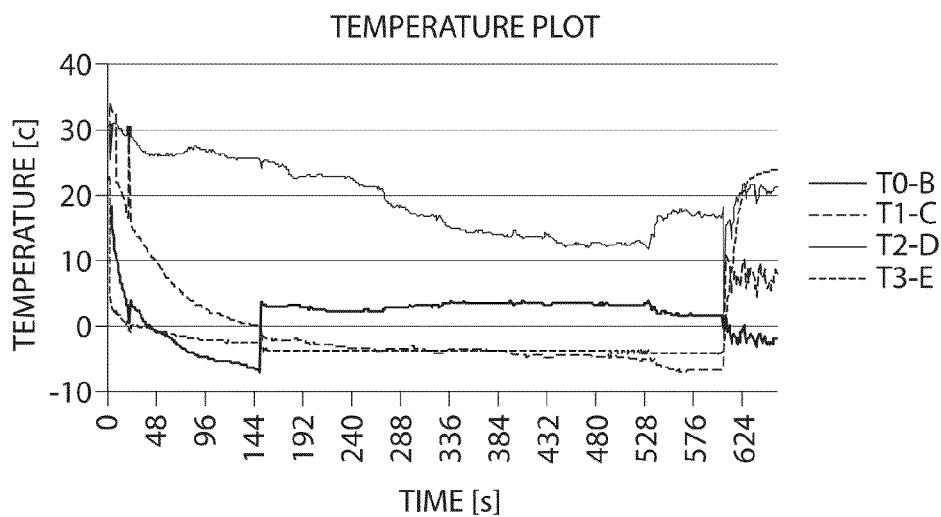
Figure 10E:
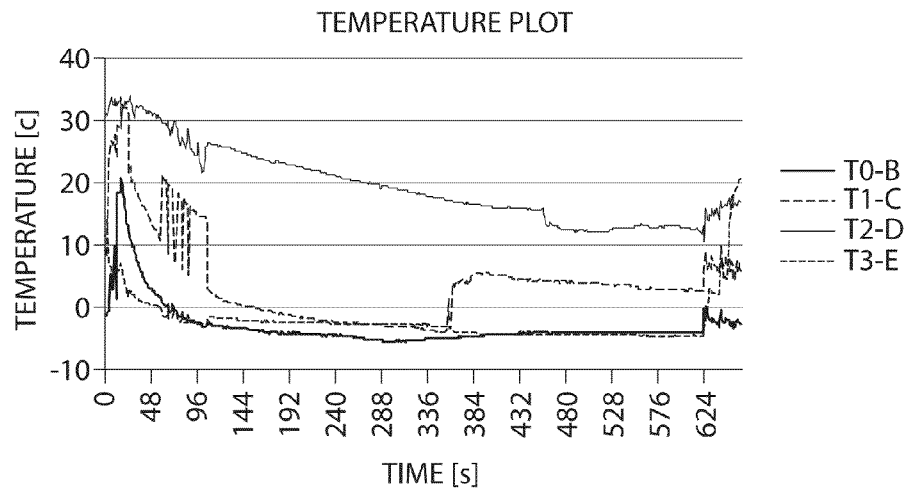
Figure 10F:
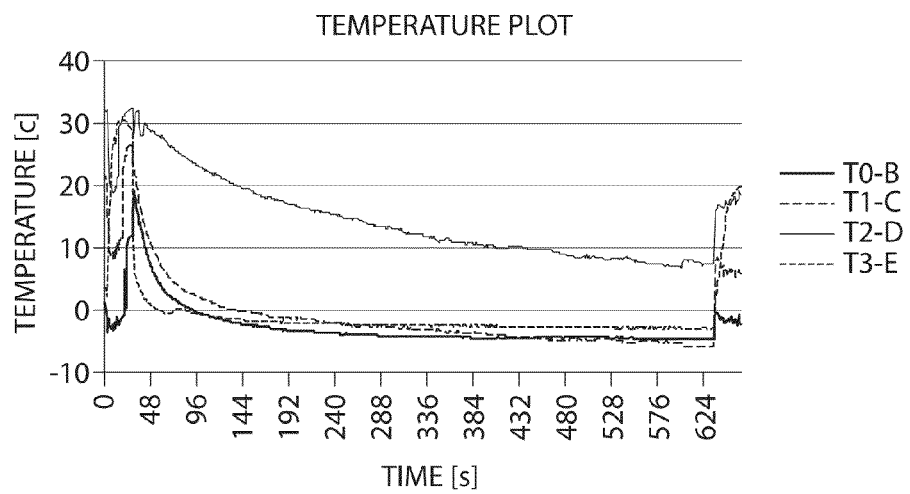
Figure 10G:
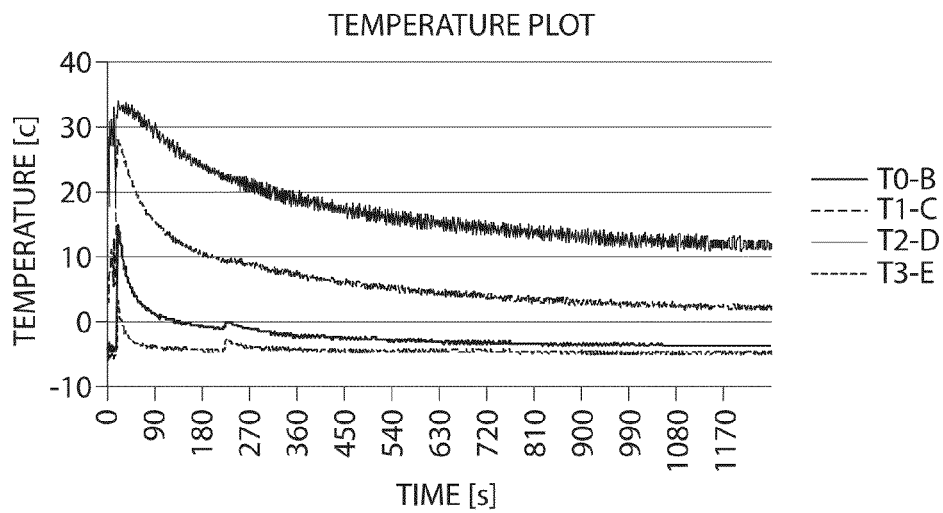
Figure 10H:
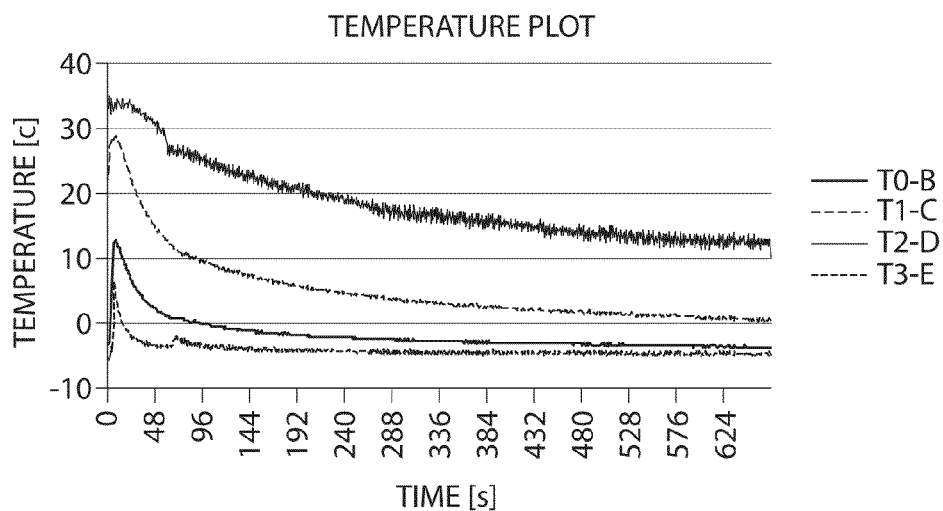
Figure 10I:
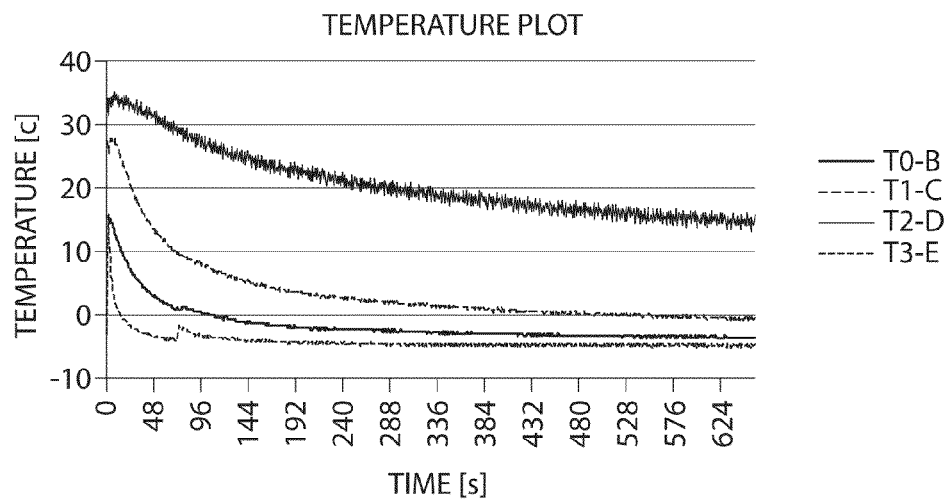
Figure 10J:
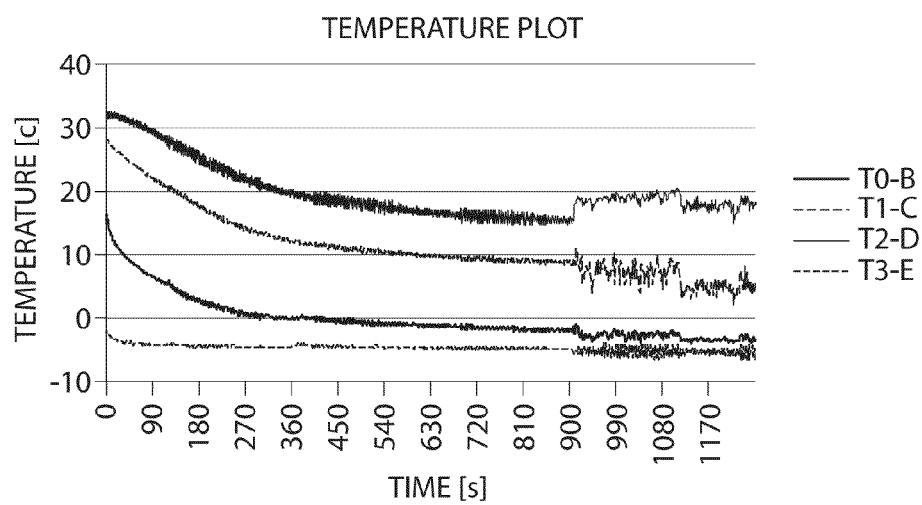

FIG. 9 depicts an image of the device for the cold exposure of Pig III. The cold copper plate 91 is brought in contact with the skin. The temperature profile within the skin during cold exposure is measured by thermocouples 92 inserted into the tissue in different depths. The device is spring loaded 93 to provide a pressure during the cold exposure.

FIGS. 10 depicts the temperature profile in various depths during the cold exposure of Pig III for different test Sites: 10A (Site 1), 10B (Site 2), 10C (Site 7), 10D (Site 11), 10E (Site 12), 10F (Site 13), 10G (Site 14), 10H (Site 15), 10I (Site 16) and 10J (Site 18). The temperature in various depths is labeled with T3-E (surface), T0-B (2-2.5 mm), T1-C (4-5 mm) and T2-D (8-10 mm).

FIG. 11 depicts an ultrasound image of test Site 11 taken 3½ months after exposure. The section below 1105 is outside the cold exposed area the section below 1106 is within the cold exposed area. The dermis 1102 can be clearly distinguished from the fat layer 1103 and the muscular layer 1104. Within the fat layer 1103 two distinct layers can be distinguished: the superficial fat layer 1103a and the deep fat layer 1103b. The ultrasound image matches well with the macroscopic cross section of the same tissue in FIG. 13c.

Figure 12A:
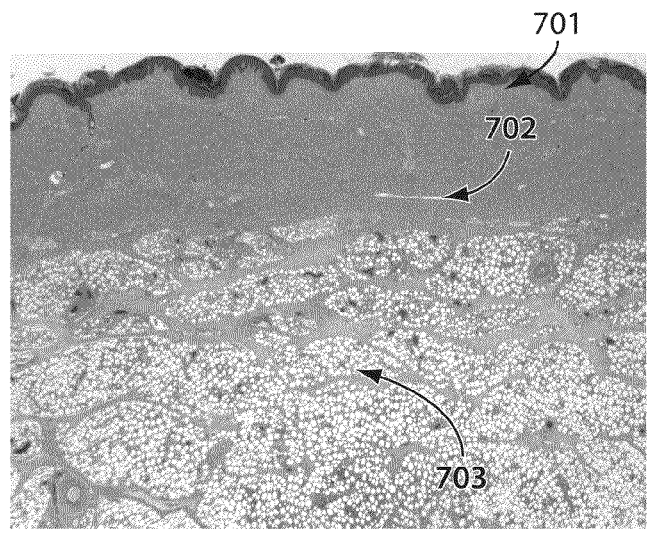
FIG. 12A, B depicts histology of test Site 8, 6 days after exposure.
Figure 12B:
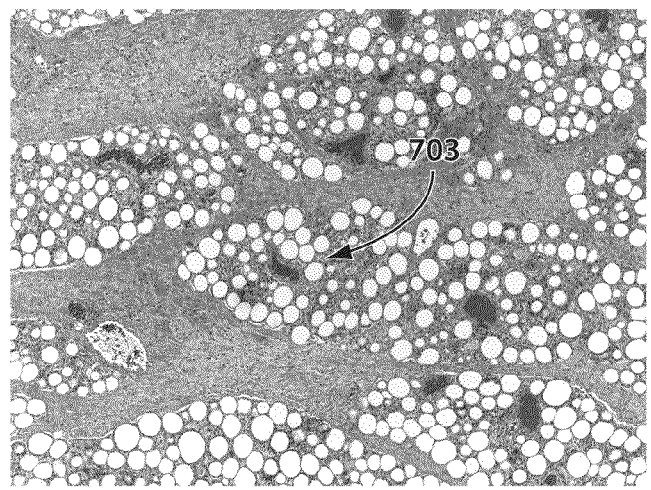
FIG. 12C, D depicts histology of test Site 9 (control).
Figure 12C:
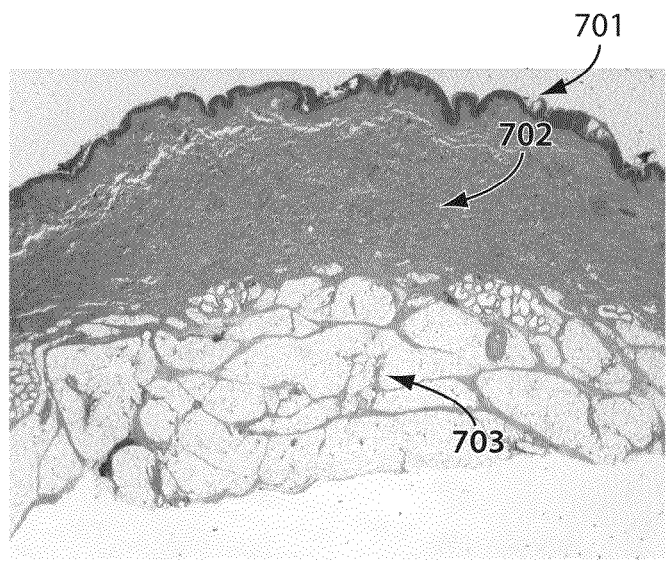
Figure 12D:
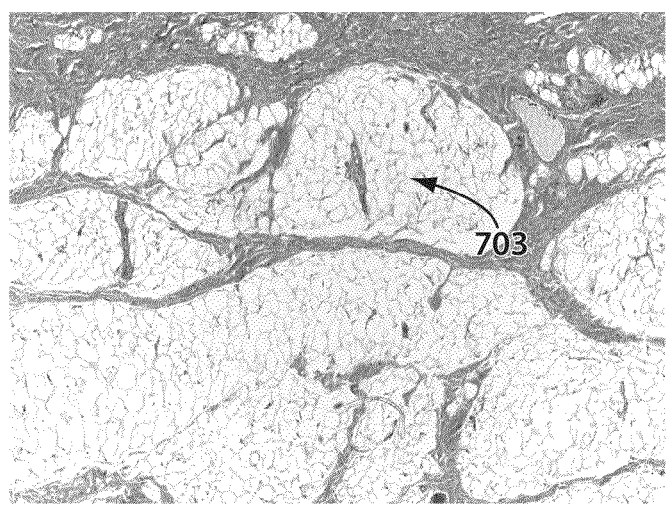

FIG. 12 depicts histology of test Site 8 (FIGS. 12A and 12B) six days after cold exposure (−7° C., 600 s) and test Site 9, which is an unexposed control (FIGS. 12C and 12D). The micrographs show an image of low power magnification (1,25×) in FIGS. 12A and 12C and a medium power magnification (5×) in FIGS. 12B and 12D. The images showing the epidermis 701, the dermis 702 and the subcutaneous fat 703. While the unexposed control exhibits normal tissue morphology, the cold-exposed tissue exhibits clear signs of panniculitis in the subcutaneous fat. Inflammatory cells have migrated into this area and the average fat cell size is decreased.

Figure 13A:
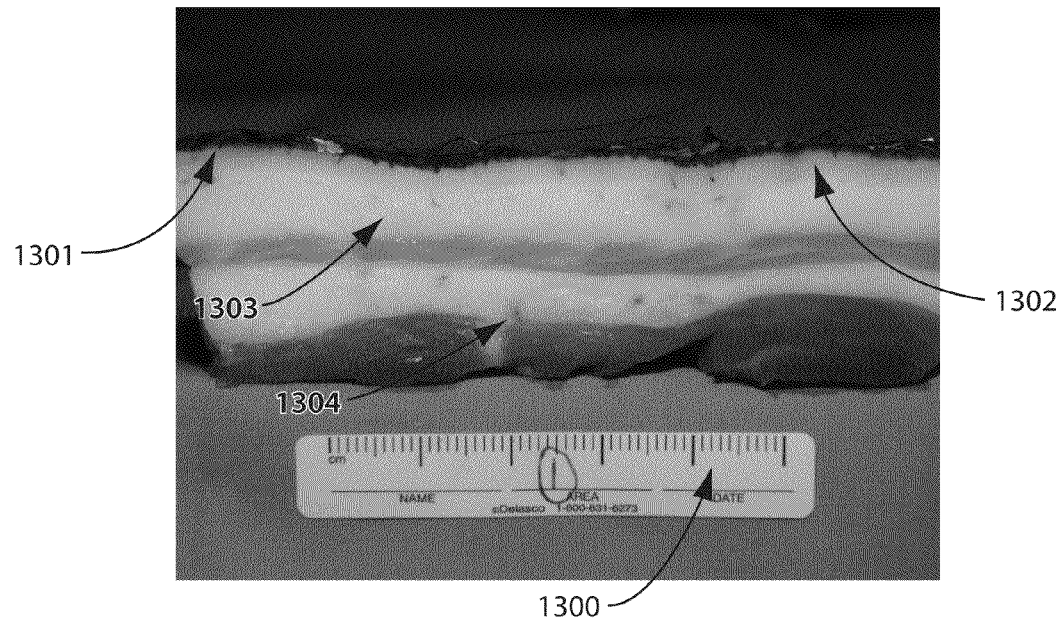
FIG. 13A, B, C, D, and E depicts macroscopic sections through the center of test Sites 1, 3, 11, 12 and 18, 3.5 months after exposure.
Figure 13B:
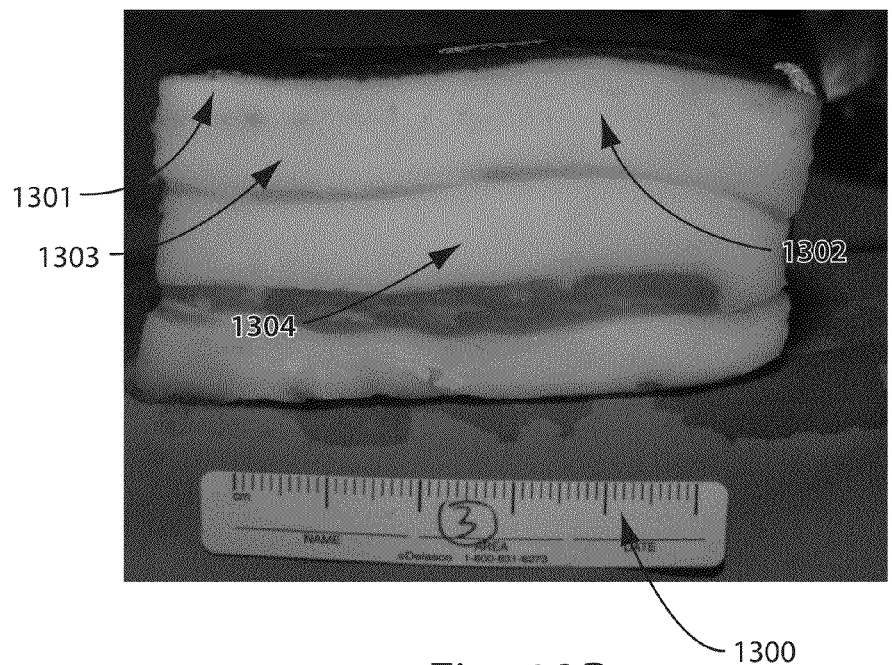
Figure 13C:
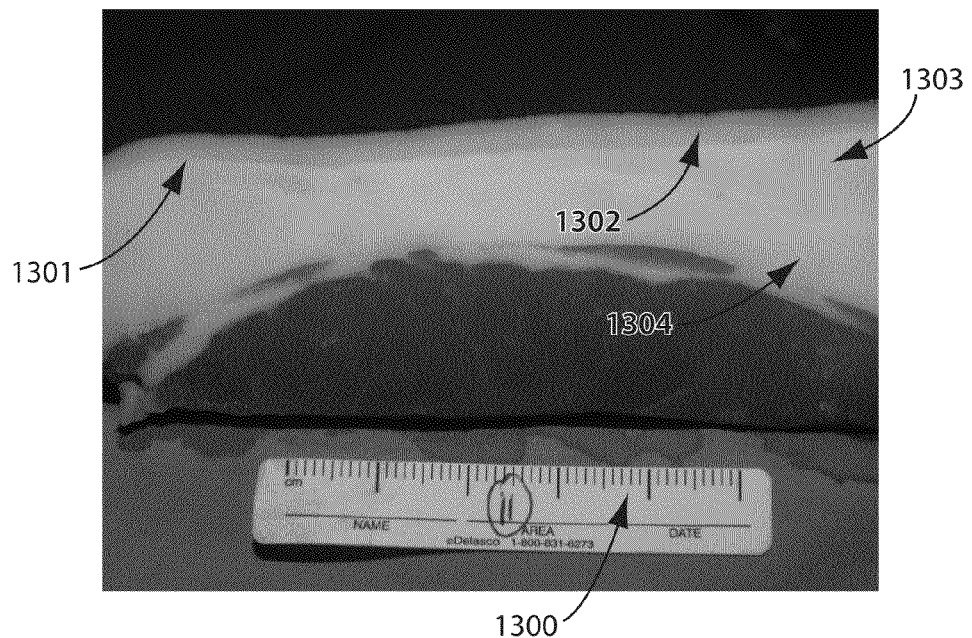
Figure 13D:
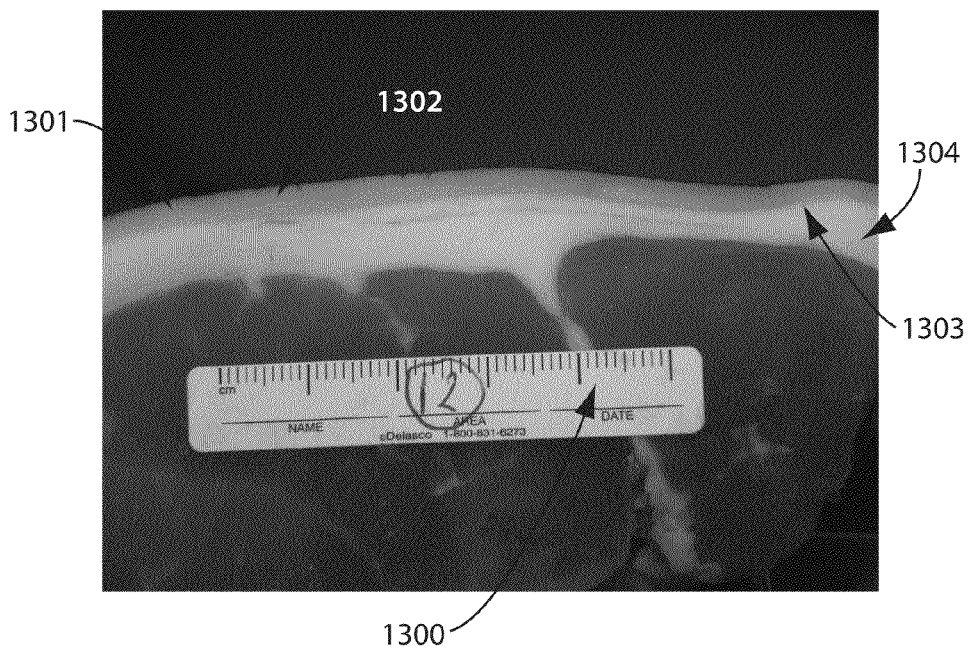
Figure 13E:
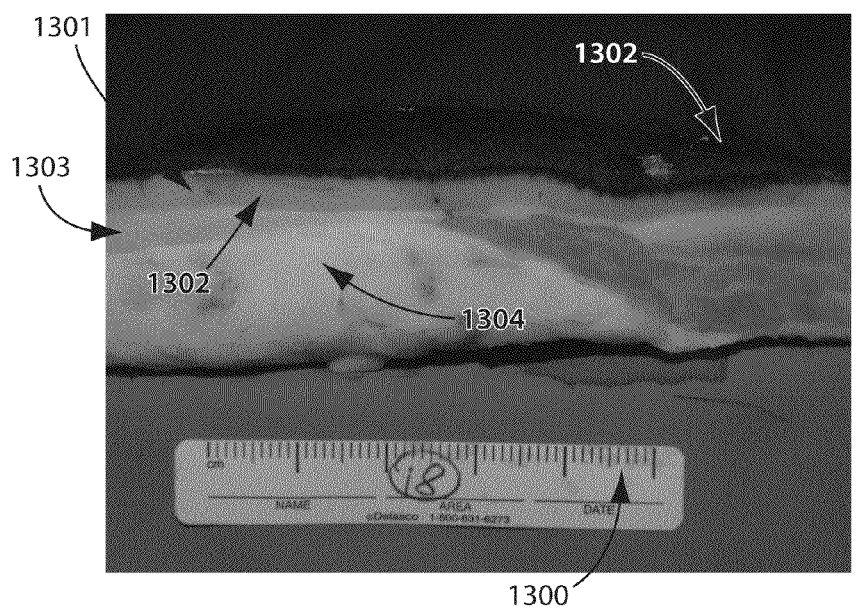

FIGS. 13 A-E depict macroscopic sections through the center of different test Sites after the pig was sacrificed, 3½ months after cold exposure: 13A (Site 1), 13B (Site 3), FIG. 13C (Site 11), FIG. 13D (Site 12) and FIG. 13E (Site 18). Each Figure exhibits a scale 1300, which has 1 cm units and 1 mm subunits. The epidermis 1301, the dermis 1302, the superficial fat layer 1303 and the deep fat layer 1304. For the unexposed control FIG. 13B no change of thickness of different layers can be seen. FIGS. 13A, 13C, 13D and 13E show the cross section of cold exposed areas, which is matched to the central 4-5 cm of tissue and non-cold exposed areas surround. A decrease of thickness within the superficial fat layer of the cold exposed areas vs. the non-cold exposed areas can be seen in all cold exposed samples. The change in % of thickness for each of the sample is listed in Table 3.

A number of embodiments of the invention have been described. Nevertheless, it will be understood that various modifications may be made without departing from the spirit and scope of the invention. Accordingly, other embodiments are within the scope of the following claims.

What is claimed is:

1. A system for removing heat from subcutaneous lipid rich cells of a subject, the system comprising:
   a cooling device having a cooling element programmed to reduce a temperature of a local region containing the lipid rich cells to between about −10° C. and about 20° C. such that lipid rich cells in the local region are reduced while non-lipid rich cells in the epidermis are generally not reduced; and
   a suction unit coupled to the cooling device to apply vacuum to the local region.

2. The system of claim 1, wherein the cooling device further comprises a detector proximate to the cooling element, and wherein the system further comprises:
   a processor in electrical communication with the detector and configured to convert electrical signals from the detector into an operating parameter; and
   a database electrically connected to the processor to store the operating parameter.

3. The system of claim 2, wherein the processor includes a control module for controlling the temperature of the local region based on the operating parameter.

4. The system of claim 2, wherein the detector is selected from the group consisting of: a temperature sensor, a thermocouple, and a thermistor.

5. The system of claim 1, further comprising a treatment interface in thermal communication with the cooling element.

6. The system of claim 5, further comprising a temperature sensor proximate to the treatment interface.

7. A system for removing heat from subcutaneous lipid rich cells of a subject, the system comprising:
   a cooling device having a cooling element for reducing a temperature of a local region containing the lipid rich cells such that lipid rich cells in the local region are reduced while non-lipid rich cells in the epidermis are generally not reduced;
   a suction unit coupled to the cooling device to apply vacuum to the local region; and
   a control unit programmed to control the operation of the cooling device to reduce the temperature within the local region to between about −10° C. and about 20° C. such that lipid rich cells in the local region are reduced while non-lipid rich cells in the epidermis are generally not reduced.

8. The system of claim 7, wherein the control unit includes:
   storage means for storing instructions for controlling the operation of the cooling device to decrease the temperature within the local region to between about −10° C. and about 20° C., such that lipid rich cells in the local region are reduced while non-lipid rich cells in the epidermis are generally not reduced; and
   a processor device programmed to read and execute the instructions stored on the storage means.

9. The system of claim 8, wherein the storage means is selected from the group consisting of: a memory device, random access memory ("RAM"), read-only memory ("ROM"), flash memory, Electrically Erasable Programmable Read Only Memory ("EEPROM"), a storage device, a hard disk, a CD-ROM, a CD-RW, a DVD-ROM, and a DVD-RW.

10. The system of claim 7, further comprising a detector proximate to the cooling element.

11. The system of claim 10, wherein the detector is selected from the group consisting of: a temperature sensor, a thermocouple, and a thermistor.

12. The system of claim 7, further comprising a treatment interface in thermal communication with the cooling element.

13. The system of claim 12, further comprising a temperature sensor proximate to the treatment interface.

14. The system of claim 7, wherein the control unit is programmed to control the operation of the cooling device to reduce the temperature within the local region to between about −10° C. and about 15° C.

15. The system of claim 7, wherein the control unit is programmed to control the operation of the cooling device to reduce the temperature within the local region to between about −10° C. and about 10° C.

16. The system of claim 7, wherein the control unit is programmed to control the operation of the cooling device to reduce the temperature within the local region to between about −10° C. and about 4° C.

17. A system for removing heat from subcutaneous lipid rich cells of a region of skin of a subject, comprising:
   a cooling device having a cooling element programmed to maintain itself at an average temperature between about −15° C. and about 15° C. in order to reduce a temperature of the region such that lipid rich cells in the region are reduced while non-lipid rich cells in the epidermis are generally not reduced; and
   a suction unit coupled to the cooling device to apply vacuum to the region.

18. The system of claim 17, wherein the cooling device further comprises a detector proximate to the cooling element, and wherein the system further comprises:
   a processor in electrical communication with the detector and configured to convert electrical signals from the detector into an operating parameter; and
   a database electrically connected to the processor to store the operating parameter.

19. The system of claim 18, wherein the processor includes a control module for controlling the temperature of the region based on the operating parameter.

20. The system of claim 18, wherein the detector is selected from the group consisting of: a temperature sensor, a thermocouple, and a thermistor.

21. The system of claim 17, further comprising a treatment interface in thermal communication with the cooling element.

22. The system of claim 21, further comprising a temperature sensor proximate to the treatment interface.

23. A system for removing heat from subcutaneous lipid rich cells of a region of skin of a subject, the system comprising:
   a cooling device having a cooling element for reducing a temperature of the region such that lipid rich cells in the region are reduced while non-lipid rich cells in the epidermis are generally not reduced;
   a suction unit coupled to the cooling device to apply vacuum to the region; and
   a control unit programmed to control the operation of the cooling device to maintain the cooling device at an average temperature between about −15° C. and about 15° C. such that lipid rich cells in the region are reduced while non-lipid rich cells in the epidermis are generally not reduced.

24. The system of claim 23, wherein the control unit includes:
   storage means for storing instructions for controlling the operation of the cooling device to maintain the cooling device at an average temperature between about −15° C. and about 15° C., such that lipid rich cells in the region are reduced while non-lipid rich cells in the epidermis are generally not reduced; and a processor device programmed to read and execute the instructions stored on the storage means.

25. The system of claim 24, wherein the storage means is selected from the group consisting of: a memory device, random access memory ("RAM"), read-only memory ("ROM"), flash memory, Electrically Erasable Programmable Read Only Memory ("EEPROM"), a storage device, a hard disk, a CD-ROM, a CD-RW, a DVD-ROM, and a DVD-RW.

26. The system of claim 23, further comprising a detector proximate to the cooling element.

27. The system of claim 26, wherein the detector is selected from the group consisting of: a temperature sensor, a thermocouple, and a thermistor.

28. The system of claim 23, further comprising a treatment interface in thermal communication with the cooling element.

29. The system of claim 28, further comprising a temperature sensor proximate to the treatment interface.

30. A system for removing heat from subcutaneous lipid rich cells of a subject, the system comprising:

a cooling device having a cooling element for reducing a temperature of a local region containing the lipid rich cells such that lipid rich cells in the local region are reduced while non-lipid rich cells in the epidermis are generally not reduced; and a control unit programmed to control the operation of the cooling device to reduce the temperature within the local region to between about −10° C. and about 10° C. such that lipid rich cells in the local region are reduced while non-lipid rich cells in the epidermis are generally not reduced.

31. The system of claim 30, wherein the control unit includes:

storage means for storing instructions for controlling the operation of the cooling device to decrease the temperature within the local region to between about −10° C. and about 10° C., such that lipid rich cells in the local region are reduced while non-lipid rich cells in the epidermis are generally not reduced; and a processor device programmed to read and execute the instructions stored on the storage means.

32. The system of claim 30, wherein the control unit is programmed to control the operation of the cooling device to reduce the temperature within the local region to between about −10° C. and about 4° C.

33. The system of claim 30, wherein the control unit includes:

storage means for storing instructions for controlling the operation of the cooling device to decrease the temperature within the local region to between about −10° C. and about 4° C., such that lipid rich cells in the local region are reduced while non-lipid rich cells in the epidermis are generally not reduced; and a processor device programmed to read and execute the instructions stored on the storage means.

34. The system of claim 30, wherein the control unit is further programmed to control the operation of the cooling device such that non-lipid rich cells in the dermis are generally not reduced.

35. The system of claim 30, wherein the cooling element has a substantially flat surface.

36. A system for removing heat from subcutaneous lipid rich cells of a region of skin of a subject, the system comprising:

a cooling device having a cooling element for reducing a temperature of the region such that lipid rich cells in the region are reduced while non-lipid rich cells in the epidermis are generally not reduced; and a control unit programmed to control the operation of the cooling device to maintain the cooling device at an average temperature between about −15° C. and about 10° C. such that lipid rich cells in the region are reduced while non-lipid rich cells in the epidermis are generally not reduced.

37. The system of claim 36, wherein the control unit includes:

storage means for storing instructions for controlling the operation of the cooling device to maintain the cooling device at an average temperature between about −15° C. and about 10° C., such that lipid rich cells in the region are reduced while non-lipid rich cells in the epidermis are generally not reduced; and a processor device programmed to read and execute the instructions stored on the storage means.

38. The system of claim 37, wherein the storage means is selected from the group consisting of: a memory device, random access memory ("RAM"), read-only memory ("ROM"), flash memory, Electrically Erasable Programmable Read Only Memory ("EEPROM"), a storage device, a hard disk, a CD-ROM, a CD-RW, a DVD-ROM, and a DVD-RW.

39. The system of claim 36, wherein the control unit is programmed to maintain the cooling device at an average temperature between about −15° C. and about 5° C.

40. The system of claim 36, wherein the control unit includes:

storage means for storing instructions for controlling the operation of the cooling device to maintain the cooling device at an average temperature between about −15° C. and about 5° C., such that lipid rich cells in the region are reduced while non-lipid rich cells in the epidermis are generally not reduced; and a processor device programmed to read and execute the instructions stored on the storage means.

41. The system of claim 36, wherein the control unit is further programmed to control the operation of the cooling device such that non-lipid rich cells in the dermis are generally not reduced.

42. The system of claim 36, wherein the cooling element has a substantially flat surface.

* * * * *